US010576184B2

(12) United States Patent
Nakamura

(10) Patent No.: US 10,576,184 B2
(45) Date of Patent: Mar. 3, 2020

(54) TUBULAR STRUCTURE, DEVICE FOR MANUFACTURING TUBULAR STRUCTURE, AND METHOD FOR MANUFACTURING TUBULAR STRUCTURE

(71) Applicant: FUJIFILM Corporation, Tokyo (JP)

(72) Inventor: Kentaro Nakamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 162 days.

(21) Appl. No.: 15/499,977

(22) Filed: Apr. 28, 2017

(65) Prior Publication Data

US 2017/0304503 A1 Oct. 26, 2017

Related U.S. Application Data

(63) Continuation of application No. PCT/JP2015/080752, filed on Oct. 30, 2015.

(30) Foreign Application Priority Data

Oct. 31, 2014 (JP) .................. 2014-222720

(51) Int. Cl.
*A61F 2/06* (2013.01)
*A61L 27/50* (2006.01)
(Continued)

(52) U.S. Cl.
CPC .............. *A61L 27/507* (2013.01); *A61F 2/06* (2013.01); *A61L 27/22* (2013.01);
(Continued)

(58) Field of Classification Search
CPC .... A61F 2/06; A61F 2/062; A61F 2/07; A61L 27/507; A61L 27/22; A61L 27/222;
(Continued)

(56) References Cited

U.S. PATENT DOCUMENTS 9,211,266 B2 * 12/2015 Iwazawa .............. A61K 9/7007
9,597,432 B2 * 3/2017 Nakamura ........... A61L 27/222
(Continued)

FOREIGN PATENT DOCUMENTS

JP 2003-24351 A 1/2003
JP 2011-130995 A 7/2011
(Continued)

OTHER PUBLICATIONS

Extended European Search Report dated Oct. 19, 2017, for European Application No. 15855417.0.
(Continued)

*Primary Examiner* — Alvin J Stewart
(74) *Attorney, Agent, or Firm* — Birch, Stewart, Kolasch & Birch, LLP

(57) ABSTRACT

An object of the present invention is to provide a cell-containing bioabsorbable tubular structure having molecular permeability, a device for manufacturing the tubular structure, and a method for manufacturing the tubular structure. According to the present invention, there is provided a tubular structure constituted with a cell structure which contains biocompatible polymer blocks and cells, in which the plurality of polymer blocks is disposed in voids between the plurality of cells.

18 Claims, 9 Drawing Sheets

Specification includes a Sequence Listing.

(51) Int. Cl.
  *A61L 27/22*  (2006.01)
  *A61L 27/36*  (2006.01)
  *A61L 27/54*  (2006.01)
  *C12N 5/00*  (2006.01)

(52) U.S. Cl.
  CPC ........... *A61L 27/3604* (2013.01); *A61L 27/54* (2013.01); *C12N 5/0068* (2013.01); *A61L 2300/80* (2013.01)

(58) Field of Classification Search
  CPC ........ A61L 27/225; A61L 27/14; A61L 27/38; A61L 27/54; A61L 27/227; A61L 27/3808; A61L 27/58
  See application file for complete search history.

(56) References Cited

U.S. PATENT DOCUMENTS

| | | | |
|---|---|---|---|
| 2005/0043585 A1* | 2/2005 | Datta | A61F 2/0077 600/153 |
| 2007/0155010 A1* | 7/2007 | Farnsworth | A61L 27/18 435/399 |
| 2008/0109070 A1* | 5/2008 | Wagner | A61L 27/3843 623/1.41 |
| 2012/0100182 A1* | 4/2012 | Mooney | A61K 39/39 424/400 |
| 2012/0165957 A1* | 6/2012 | Everland | A61F 2/0045 623/23.72 |
| 2012/0329157 A1 | 12/2012 | Nakamura | |
| 2013/0040891 A1 | 2/2013 | Okamoto et al. | |
| 2013/0071441 A1* | 3/2013 | Iwazawa | A61K 9/7007 424/400 |
| 2015/0352252 A1* | 12/2015 | Nakamura | A61L 27/222 424/422 |
| 2017/0095595 A1* | 4/2017 | Nakamura | A61L 27/00 |

FOREIGN PATENT DOCUMENTS

| | | |
|---|---|---|
| JP | WO 2011/108517 A1 | 9/2011 |
| JP | 2014-12114 A | 1/2014 |
| WO | WO 01/05333 A1 | 1/2001 |
| WO | WO 2011/102363 A1 | 8/2011 |
| WO | WO 2014/133081 A1 | 9/2014 |

OTHER PUBLICATIONS

Japanese Office Action, dated Dec. 26, 2017, for corresponding Japanese Application No. 2016-556657, with an English machine translation.
Abbott et al., "Effect of compliance mismatch on vascular graft patency", Journal of Vascular Surgery, 1987, vol. 5, No. 2, pp. 376-382.
Hashi et al., "Antithrombogenic property of bone marrow mesenchymal stem cells in nanofibrous vascular grafts", Proc. Natl. Acad. Sci. USA, Jul. 17, 2007, vol. 104, No. 29, pp. 11915-11920.
International Search Report for PCT/JP2015/080752 dated Jan. 12, 2016.
Krawiec et al., "Adult stem cell-based tissue engineered blood vessels: A review", Biomaterials, 2012, vol. 33, No. 12, pp. 3388-3400.
Written Opinion of the International Searching Authority for PCT/JP2015/080752 (PCT/ISA/237) dated Jan. 12, 2016.
Zhao et al., "A novel strategy to engineer small-diameter vascular grafts from marrow-derived mesenchymal stem cells", Artificial Organs, 2012, vol. 36, No. 1, pp. 93-101.
International Preliminary Report on Patentability and Written Opinion of the International Searching Authority (Forms PCT/IB/338, PCT/IB/373, PCT/ISA/237 and PCT/IB/326), dated May 11, 2017, issued in International Application No. PCT/JP2015/080752, together with an English translation.
Rhee et al., "A Study of the Wall Shear Rate Distribution Near the End-to-End Anastomosis of a Rigid Graft and a Compliant Artery," Journal of Biomechanics, vol. 27, No. 3, 1994, pp. 329-338.
Weston et al., "Compliance and Diameter Mismatch Affect the Wall Shear Rate Distribution Near an End-to-End Anastomosis," Journal of Biomechanics, vol. 29, No. 2, 1996, pp. 187-198.
European Office Action, dated Dec. 21, 2018, for corresponding European Application No. 15855417.0.
Japanese Office Action, dated Jul. 31, 2018, for corresponding Japanese Application No. 2016-556657, with an English machine translation.
Office Action and Search Report issued in CN 201580059118.4 dated Jul. 16, 2019 (with English-language Translation).
English machine translation of the Japanese Office Action, dated Dec. 24, 2019, for Japanese Application No. 2018-204834.

\* cited by examiner

FIG. 4A
FIG. 4B            FIG. 4C
    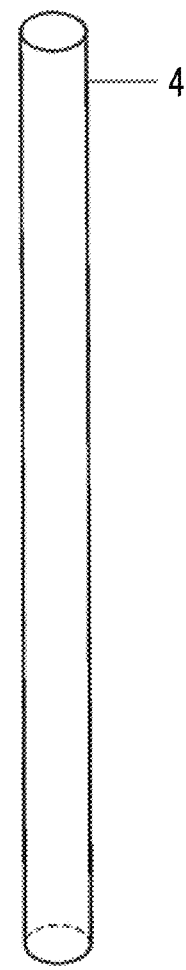

SEQUENCE LISTING

```
<160> NUMBER OF SEQ ID NOS: 10

<210> SEQ ID NO 1
<211> LENGTH: 571
<212> TYPE: PRT
<213> ORGANISM: Artificial Sequence
<220> FEATURE:
<223> OTHER INFORMATION: Synthetic:  Recombinant

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160
```

```
Leu Pro Gly Pro Lys Gly Glu Arg Gly Asp Ala Gly Pro Lys Gly Ala
            165                 170                 175
Asp Gly Ala Pro Gly Lys Asp Gly Val Arg Gly Leu Ala Gly Pro Pro
        180                 185                 190
Gly Ala Pro Gly Leu Gln Gly Ala Pro Gly Leu Gln Gly Met Pro Gly
    195                 200                 205
Glu Arg Gly Ala Ala Gly Leu Pro Gly Pro Lys Gly Glu Arg Gly Asp
210                 215                 220
Ala Gly Pro Lys Gly Ala Asp Gly Ala Pro Gly Ala Pro Gly Leu Gln
225                 230                 235                 240
Gly Met Pro Gly Glu Arg Gly Ala Ala Gly Leu Pro Gly Pro Lys Gly
            245                 250                 255
Glu Arg Gly Asp Ala Gly Pro Lys Gly Ala Asp Gly Ala Pro Gly Lys
        260                 265                 270
Asp Gly Val Arg Gly Leu Ala Gly Pro Ile Gly Pro Pro Gly Glu Arg
    275                 280                 285
Gly Ala Ala Gly Leu Pro Gly Pro Lys Gly Glu Arg Gly Asp Ala Gly
290                 295                 300
Pro Lys Gly Ala Asp Gly Ala Pro Gly Lys Asp Gly Val Arg Gly Leu
305                 310                 315                 320
Ala Gly Pro Ile Gly Pro Pro Gly Pro Ala Gly Ala Pro Gly Ala Pro
            325                 330                 335
Gly Leu Gln Gly Met Pro Gly Glu Arg Gly Ala Ala Gly Leu Pro Gly
        340                 345                 350
Pro Lys Gly Glu Arg Gly Asp Ala Gly Pro Lys Gly Ala Asp Gly Ala
    355                 360                 365
Pro Gly Lys Asp Gly Val Arg Gly Leu Ala Gly Pro Pro Gly Ala Pro
370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
            405                 410                 415
Lys Gly Ala Asp Gly Ala Pro Gly Ala Pro Gly Leu Gln Gly Met Pro
        420                 425                 430
Gly Glu Arg Gly Ala Ala Gly Leu Pro Gly Pro Lys Gly Glu Arg Gly
    435                 440                 445
Asp Ala Gly Pro Lys Gly Ala Asp Gly Ala Pro Gly Lys Asp Gly Val
450                 455                 460
Arg Gly Leu Ala Gly Pro Ile Gly Pro Gly Glu Arg Gly Ala Ala
465                 470                 475                 480
Gly Leu Pro Gly Pro Lys Gly Glu Arg Gly Asp Ala Gly Pro Lys Gly
            485                 490                 495
Ala Asp Gly Ala Pro Gly Lys Asp Gly Val Arg Gly Leu Ala Gly Pro
        500                 505                 510
Ile Gly Pro Pro Gly Pro Ala Gly Ala Pro Gly Ala Pro Gly Leu Gln
    515                 520                 525
Gly Met Pro Gly Glu Arg Gly Ala Ala Gly Leu Pro Gly Pro Lys Gly
530                 535                 540
Glu Arg Gly Asp Ala Gly Pro Lys Gly Ala Asp Gly Ala Pro Gly Lys
545                 550                 555                 560
Asp Gly Val Arg Gly Leu Ala Gly Pro Pro Gly
            565                 570
```

```
<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 7
```

```
Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 10

Glu Arg Gly Asp
1
```

TUBULAR STRUCTURE, DEVICE FOR MANUFACTURING TUBULAR STRUCTURE, AND METHOD FOR MANUFACTURING TUBULAR STRUCTURE

CROSS-REFERENCE TO RELATED APPLICATIONS

The present application is a continuation of PCT/JP2015/080752 filed on Oct. 30, 2015 and claims priority under 35 U.S.C. § 119 of Japanese Patent Application No. 222720/2014 filed on Oct. 31, 2014.

REFERENCE TO SEQUENCE LISTING SUBMITTED VIA EFS-WEB

This application includes an electronically submitted sequence listing in .txt format. The .txt file contains a sequence listing entitled "2017-07-10_Sequence_Listing_2870-0664PUS1.txt" created on Jul. 8, 2017 and is 7,191 bytes in size. The sequence listing contained in this .txt file is part of the specification and is hereby incorporated by reference herein in its entirety.

BACKGROUND OF THE INVENTION

1. Field of the Invention

The present invention relates to a tubular structure constituted with a cell structure containing biocompatible polymer blocks and cells. The present invention also related to a device for manufacturing the tubular structure and a method for manufacturing the tubular structure.

2. Description of the Related Art

In a biological body, tissues having a tubular structure such as blood vessels, a digestive tract, a ureter, and lymphatic vessels function as important tissues. Examples of particularly important tubular structures include blood vessels. A large number of artificial blood vessels has been developed because they are required as a substitute for diseases or surgery. Examples of the artificial blood vessels that are becoming increasingly widespread in the clinical application include artificial blood vessels using a non-biodegradable synthetic polymer such as polytetrafluoroethylene (PTFE).

It's been a long time since an attempt was made to develop a hybrid artificial blood vessel by endothelializing an artificial blood vessel formed of a synthetic polymer by using cells. The endothelization of an artificial blood vessel by using cells was found to be able to impart non-thrombogenic properties, and this can arise an expectation of an effect of maintaining patency.

There is a report relating to compliance mismatch between a transplanted blood vessel and a biological artery in an anastomotic portion (Aboot, W. M.; Megerman, J.; Hasson, J. E.; L'ltalien, G.; Warnock, O. F., J. Vasc. Surg. 5 (2): 376-382; 1987). Furthermore, it is known that, in an anastomotic portion between an artificial blood vessel and a biological artery, a portion where blood flow separates and stagnates occurs, and stress concentration in the anastomotic portion causes anastomotic occlusion (Weston, M. W.; Rhee, K., Tarbell, J. M., J. Biomech. 29(2): 187-198; 1996 and Rhee, K.; Tarbell, J. M., J. Biomech. 27(3): 329-338; 1994). WO2011/108517A describes a cell structure which contains biocompatible polymer blocks and cells, in which the plurality of polymer blocks is disposed in voids between the plurality of cells. In the cell structure described in WO2011/108517A, nutrients can be delivered to the inside of the cell structure from the outside. The cell structure has a sufficient thickness, and the cells homogenously exist in the structure. In examples of WO2011/108517A, high cell viability is proved using polymer blocks formed of a recombinant gelatin or natural gelatin material.

SUMMARY OF THE INVENTION

It is known that an artificial blood vessel formed of a synthetic polymer is easily clogged due to occlusion, stenosis, or the like caused by thrombi formed on the surface of the material, particularly when the blood vessel has a small caliber. In addition, in a case where the artificial blood vessel is used for a subject such as a child who is growing, the blood vessel that does not grow by itself is inappropriate. As an attempt to solve the above problems, a hybrid artificial blood vessel is also reported which is obtained by endothelializing an artificial blood vessel formed of a synthetic polymer material by using cells, but this has a problem of anastomotic occlusion in an anastomotic portion between the artificial blood vessel and a biological artery. In this respect, there is a demand for a cell-containing bio-artificial blood vessel which needs to change its size in a subject such as a child who is growing, does not contain a non-bioabsorbable material, and can easily substitute a biological tissue.

It is known that the wall of the general artery and aorta has a thickness of about 1 to 2 mm. In a case where a tubular structure having a wall with a thickness of 1 to 2 mm is formed using only cells, molecular permeability which is an important role of a tubular structure in a biological body such as a blood vessel is impaired. An artificial blood vessel is required to have an ability to allow the permeation of an appropriate molecule from the wall surface of the tubular structure. In this respect, in the tubular structure formed only of cells, even a molecule with a low molecular weight cannot permeate the wall surface thereof, and hence the tubular structure is inappropriate for being used in a biological body. A non-bioabsorbable artificial blood vessel constituted only with a synthetic polymer such as ePTFE has low molecular permeability and cannot provide a required function.

Although WO2011/108517A describes a cell structure containing biocompatible polymer blocks and cells, it does not states the formation of a tubular structure such as an artificial blood vessel.

An object of the present invention is to provide a cell-containing bioabsorbable tubular structure having molecular permeability. Another object of the present invention is to provide a device for manufacturing the tubular structure and a method for manufacturing the tubular structure.

As a result of conducting intensive investigation for achieving the aforementioned objects, the inventors of the present invention obtained knowledge that, by culturing a cell structure, which contains biocompatible polymer blocks and cells and in which the plurality of biocompatible polymer blocks is disposed in voids between the plurality of cells, in a device having a mold for manufacturing a tubular structure, a tubular structure can be manufactured which has high ability to allow a molecule to permeate the tubular structure from the inner wall thereof and has shape maintainability. The present invention was accomplished based on the knowledge.

That is, according to the present invention, the following inventions are provided.

(1) A tubular structure comprising a cell structure containing biocompatible polymer blocks and cells, in which the plurality of polymer blocks is disposed in voids between the plurality of cells.

(2) The tubular structure described in (1) that is an artificial blood vessel.

(3) The tubular structure described in (1) or (2), in which the cell structure contains the biocompatible polymer blocks in an amount of equal to or greater than 0.0000001 μg and equal to or less than 1 μg per cell.

(4) The tubular structure described in any one of (1) to (3), in which each of the biocompatible polymer blocks has a size of equal to or greater than 10 μm and equal to or less than 300 μm.

(5) The tubular structure described in any one of (1) to (4) that has an inner diameter of equal to or greater than 1 mm and less than 6 mm, an outer diameter of equal to or greater than 3 mm and equal to or less than 10 mm, and a length of equal to or greater than 5 mm and equal to or less than 300 mm.

(6) The tubular structure described in any one of (1) to (5), in which the biocompatible polymer blocks are formed of a recombinant peptide.

(7) The tubular structure described in (6), in which the recombinant peptide is any of a peptide having an amino acid sequence described in SEQ ID NO: 1; a biocompatible peptide having an amino acid sequence obtained by the deletion, substitution, or addition of one or plural amino acids in the amino acid sequence described in SEQ ID NO: 1; or a biocompatible peptide having an amino acid sequence which shares a sequence identity of equal to or higher than 80% with the amino acid sequence described in SEQ ID NO: 1.

(8) The tubular structure described in any one of (1) to (7), in which in the biocompatible polymer blocks, the biocompatible polymer is cross-linked by heat, ultraviolet rays, or an enzyme.

(9) The tubular structure described in any one of (1) to (8), in which the biocompatible polymer blocks are in the form of granules obtained by pulverizing a porous substance of the biocompatible polymer.

(10) A device for manufacturing the tubular structure described in any one of (1) to (9), comprising a base portion that has a cylindrical hollow area for forming an external lateral surface of a tubular structure constituted with a cell structure, a core receiving portion that exists on the inside of the hollow area, and a cylindrical core portion for forming an internal lateral surface of the tubular structure, a top surface of the base portion is a flat surface, the hollow area is provided from the top surface of the base portion along a direction perpendicular to the flat surface as the top surface of the base portion, the core portion is held by the core receiving portion, at least a portion of the core portion is provided in the hollow area along a direction perpendicular to a direction of the flat surface of the base portion, the center of a diameter of the cylindrical shape of the hollow area is the same as the center of a diameter of the cylindrical shape of the core portion, the diameter of the cylindrical shape of the core portion is smaller than the diameter of the cylindrical shape of the hollow area, the core receiving portion has a through hole for holding the core portion in a central portion and one or more penetration areas, which penetrate the core receiving portion from a top surface to a bottom surface thereof, in a peripheral portion, and a bottom surface of the base portion has a structure in which when the base portion is installed in a container containing a medium, a medium component contained in the medium can enter the inside of the hollow area from an inlet on a bottom surface side of the penetration areas of the core receiving portion.

(11) The device described in (10), in which the bottom surface of the base portion has a shape having an area which contacts an installation surface when the base portion is installed on the installation surface and an area which does not contact the installation surface, and the inlet on the bottom surface side of the penetration areas of the core receiving portion is provided in the area which does not contact the installation surface.

(12) The device described in (10) or (11), in which the diameter of the cylindrical shape of the core portion is equal to or greater than 1 mm and less than 6 mm, and the diameter of the cylindrical shape of the hollow area is equal to or greater than 3 mm and equal to or less than 10 mm.

(13) The device described in any one of (10) to (12), in which either or both of the core portion and a portion forming the hollow area have a hollow mesh shape.

(14) A method for manufacturing the tubular structure described in any one of (1) to (9), comprising a step of fusing a plurality of cell structures in which the biocompatible polymer blocks are disposed in voids of a plurality of cells.

(15) The method described in (14), in which the cell structures are fused by culturing the plurality of cell structures, in which biocompatible polymer blocks are disposed in voids of a plurality of cells, in a device having a mold for forming a tubular structure.

(16) The method described in (14) or (15), in which the device having a mold for forming a tubular structure is the device described in any one of (10) to (13).

The tubular structure of the present invention has an ability to allow molecules to permeate the tubular structure from the inner wall thereof and has shape maintainability. The device of the present invention is useful for manufacturing the tubular structure of the present invention. According to the manufacturing method of the present invention, it is possible to manufacture a tubular structure having a high ability to allow molecules to permeate the tubular structure from the inner wall thereof and has shape maintainability.

BRIEF DESCRIPTION OF THE DRAWINGS

FIGS. 4A-4C show an example of the structure of a core portion.

DESCRIPTION OF THE PREFERRED EMBODIMENTS

Figure 1A:
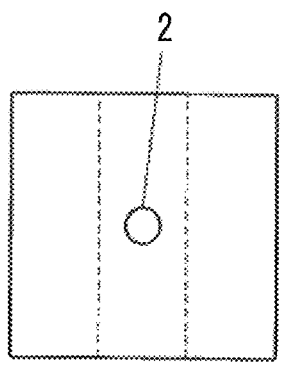
FIGS. 1A-1E show an example of the structure of a base portion.

Hereinafter, embodiments of the present invention will be specifically described.

[Tubular Structure]

The tubular structure of the present invention is constituted with a cell structure containing biocompatible polymer blocks and cells, in which the plurality of polymer blocks is disposed in voids between the plurality of cells. In the present specification, the cell structure used in the present invention will be referred to as a mosaic cell mass (cell mass in the form of mosaic) in some cases.

The tubular structure of the present invention is a structure having molecular permeability and a shape maintaining performance which makes it difficult for the shape of the tubular structure to change after formation of the structure. For example, the tubular structure can be used as an artificial blood vessel. It is a totally unexpected marked effect that the cell structure, which contains biocompatible polymer blocks and cells and in which the plurality of polymer blocks is disposed in voids between the plurality of cells, has the aforementioned performance, particularly, high molecular permeability. Although WO2011/108517A describes a cell structure which contains biocompatible polymer blocks and cells and in which the plurality of polymer blocks is disposed in voids between the plurality of cells, the document describes neither the formation of a tubular structure nor the ability to allow a molecule to permeate the tubular structure from the inner wall thereof.

(1) Biocompatible Polymer Blocks

The cell structure used in the present invention contains biocompatible polymer blocks. The biocompatible polymer blocks will be described below.

(1-1) Biocompatible Polymer

"Biocompatible" means that the polymer does not cause a markedly harmful reaction such as a prolonged or chronic inflammatory reaction when the polymer contacts a biological body. The biocompatible polymer used in the present invention is not particularly limited regarding whether or not the polymer degrades in a biological body, as long as the polymer is biocompatible. However, the biocompatible polymer is preferably a biodegradable polymer. Specific examples of non-biodegradable materials include polytetrafluoroethylene (PTFE), polyurethane, polypropylene, polyester, vinyl chloride, polycarbonate, acryl, stainless steel, titanium, silicone, 2-methacryloyloxyethyl phosphorylcholine (MPC), and the like. Specific examples of biodegradable materials include a polypeptide such as a recombinant peptide (for example, gelatin or the like which will be described below), polylactic acid, polyglycolic acid, a lactic acid.glycolic acid copolymer (PLGA), hyaluronic acid, glycosaminoglycan, proteoglycan, chondroichin, cellulose, agarose, carboxymethyl cellulose, chitin, chitosan, and the like. Among these, a recombinant peptide is particularly preferable. These biocompatible polymers may be treated such that the cell adhesiveness thereof is improved. Specifically, it is possible to use the method such as "coating a substrate surface with a cell-adhesive matrix (fibronectin, hydronectin, or laminin) or a peptide having a cell-adhesive sequence (an RGD sequence, an LDV sequence, an REDV sequence, a YIGSR sequence, a PDSGR sequence, an RYV-VLPR sequence, an LGTIPG sequence, an RNIAEIIKDI sequence, an IKVAV sequence, an LRE sequence, a DGEA sequence, and an HAV sequence expressed by one-letter amino acid notation)", "amination or cationization of a substrate surface", "a hydrophilization treatment of a substrate surface by a plasma treatment or corona discharge".

The type of the polypeptide containing a recombinant peptide is not particularly limited as long as it is biocompatible. The polypeptide is preferably, for example, gelatin, collagen, elastin, fibronectin, pronectin, laminin, tenascin, fibrin, fibroin, entactin, thrombospondin, or retronectin, and most preferably gelatin, collagen, or atelocollagen. The gelatin used in the present invention is preferably natural gelatin or recombinant gelatin, and more preferably recombinant gelatin. The natural gelatin mentioned herein refers to gelatin made of naturally occurring collagen. The recombinant gelatin will be described later in the present specification.

The value of hydrophilicity, "1/IOB" value, of the biocompatible polymer used in the present invention is preferably 0 to 1.0, more preferably 0 to 0.6, and even more preferably 0 to 0.4. IOB is an index of hydropathicity based on the organic conception diagram showing the polarity/non-polarity of organic compounds that is suggested by Atsushi Fujita, and the details thereof are explained in, for example, "Pharmaceutical Bulletin", vol. 2, 2, pp. 163-173 (1954)", "Domain of Chemistry" vol. 11, 10, pp. 719-725 (1957), "Fragrance Journal", vol. 50, pp. 79-82 (1981), and the like. In brief, to obtain the organic conception diagram, methane ($CH_4$) is regarded as an origin of all of the organic compounds, and all of the other compounds are regarded as derivatives of methane. Then, certain values are set for the number of carbon atoms, substituents, transformation portions, rings, and the like, and the scores are added up to determine an organic value (OV) and an inorganic value (IV). By plotting the values on a graph in which the X-axis and the Y-axis show the organic value and the inorganic value respectively, the organic conception diagram is obtained. IOB in the organic conception diagram is a ratio of the inorganic value (IV) to the organic value (OV) in the organic conception diagram, that is, "inorganic value (IV)/organic value (OV)". For details of the organic conception diagram, see "New edition of Organic Conception Diagram—fundamental and application—" (Yoshio Kouda et al., SANKYO SHUPPAN Co., Ltd., 2008). In the present specification, hydropathicity is indicated by the "1/IOB" value which is the reciprocal of JOB. The smaller the "1/IOB" value (the closer the value is to 0), the more the polymer is hydrophilic.

By setting the "1/IOB" value of the polymer used in the present invention to fall into the above range, the hydrophilicity becomes high, the water absorption properties are improved, and hence nutritional components are effectively held. Presumably, as a result, the setting of the value as described above may contribute to the stabilization and viability of the cells in the cell structure (mosaic cell mass) of the present invention.

In a case where the biocompatible polymer used in the present invention is a polypeptide, the hydropathicity index represented by a value of Grand average of hydropathicity (GRAVY) thereof is preferably equal to or less than 0.3 and equal to or greater than −9.0, and more preferably equal to or less than 0.0 and equal to or greater than −7.0. The value of Grand average of hydropathicity (GRAVY) can be obtained by the methods of "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appel R. D., Bairoch A.; ExPASy: the proteomics server for in-depth protein knowledge and analysis; Nucleic Acids Res. 31:3784-3788 (2003)."

By setting the GRAVY value of the polymer used in the present invention to fall into the above range, the hydrophilicity becomes high, the water absorption properties are improved, and hence nutritional components are effectively held. Presumably, as a result, the setting of the value as described above may contribute to the stabilization and viability of the cells in the cell structure (mosaic cell mass) of the present invention.

(1-2) Cross-Linking

The biocompatible polymer used in the present invention may or may not be cross-linked, but is preferably cross-linked. The use of the cross-linked biocompatible polymer brings about an effect of preventing the polymer from instantaneously degrading when being cultured in a medium and when being transplanted into a biological body. As general cross-linking methods, thermal cross-linking, cross-linking by using aldehydes (for example, formaldehyde or glutaraldehyde), cross-linking by using a condensing agent (carbodiimide, cyanamide, or the like), enzymatic cross-linking, photo-cross-linking, ultraviolet cross-linking, hydrophobic interaction, hydrogen bonding, ionic interaction, and the like are known. In the present invention, it is preferable to use a cross-linking method that does not use glutaraldehyde. In the present invention, it is more preferable to use a cross-linking method that does not use aldehydes or a condensing agent. That is, the biocompatible polymer blocks in the present invention are preferably biocompatible polymer blocks that do not contain glutaraldehyde, and more preferably biocompatible polymer blocks that do not contain aldehydes or a condensing agent. The cross-linking method used in the present invention is more preferably thermal cross-linking, ultraviolet cross-linking, or enzymatic cross-linking, and particularly preferably thermal cross-linking.

In a case where cross-linking is performed using an enzyme, the enzyme is not particularly limited as long as it acts to cross-link polymer materials. The cross-linking can be performed preferably using transglutaminase and laccase and most preferably using transglutaminase. Specific examples of proteins enzymatically cross-linked by transglutaminase are not particularly limited as long as they are proteins having a lysine residue and a glutamine residue. The transglutaminase may be derived from mammals or microorganisms. Specific examples thereof include an ACTIVA series manufactured by AJINOMOTO CO., INC., mammal-derived transglutaminase on the sale as a reagent such as transglutaminase derived from the guinea pig liver, goat-derived transglutaminase, or rabbit-derived transglutaminase manufactured by ORIENTAL YEAST Co., Ltd., Upstate USA Inc., and Biodesign International, Inc., a blood clotting factor derived from a human being (Factor XIIIa, manufactured by Haematologic Technologies, Inc.), and the like.

The reaction temperature at the time of performing the cross-linking (for example, thermal cross-linking) is not particularly limited as long as cross-linking can be performed. The reaction temperature is preferably −100° C. to 500° C., more preferably 0° C. to 300° C., even more preferably 50° C. to 300° C., still more preferably 100° C. to 250° C., and yet more preferably 120° C. to 200° C.

(1-3) Recombinant Gelatin

The recombinant gelatin mentioned in the present invention means a polypeptide or a protein-like substance that is prepared by gene recombination technique and has an amino acid sequence analogous to gelatin. The recombinant gelatin which can be used in the present invention preferably has a repeating sequence represented by Gly-X-Y (X and Y each independently represent a certain amino acid) unique to collagen. A plurality of Gly-X-Y sequences may be the same as or different from each other. It is preferable that a cell-adhesive signal has two or more of the sequences in a single molecule. As the recombinant gelatin used in the present invention, it is possible to use recombinant gelatin having an amino acid sequence derived from a partial amino acid sequence of collagen. For example, it is possible to use those described in EP1014176, U.S. Pat. No. 6,992,172, WO2004/85473, WO2008/103041, and the like, but the present invention is not limited thereto. As the recombinant gelatin used in the present invention, recombinant gelatin of the following aspect is preferable.

The recombinant gelatin has excellent biocompatibility due to the performance intrinsic to the natural gelatin, has no risk of bovine spongiform encephalopathy (BSE) because it is not naturally occurring, and is excellently noninfectious. Furthermore, the recombinant gelatin is more homogeneous than the natural gelatin. In addition, because the sequence is determined, by cross-linking or the like, the recombinant gelatin can be accurately designed with a small fluctuation regarding the strength and degradability.

The molecular weight of the recombinant gelatin is not particularly limited, but is preferably equal to or greater than 2 kDa and equal to or less than 100 kDa, more preferably equal to or greater than 2.5 kDa and equal to or less than 95 kDa, even more preferably equal to or greater than 5 kDa and equal to or less than 90 kDa, and most preferably equal to or greater than 10 kDa and equal to or less than 90 kDa.

It is preferable that the recombinant gelatin has a repeating sequence represented by Gly-X-Y unique to collagen. Herein, a plurality of Gly-X-Y sequences may be the same as or different from each other. In Gly-X-Y, Gly represents glycine, and X and Y represent a certain amino acid (preferably a certain amino acid other than glycine). The sequence represented by Gly-X-Y unique to collagen is a partial structure in an amino acid composition and sequence of gelatin•collagen that is extremely specific compared to other proteins. In this portion, glycine takes up about ⅓ of the entire sequence, and in the amino acid sequence, one of the three amino acids is repeated. Glycine is the simplest amino acid, the disposition thereof in a molecular chain is less restricted, and makes a great contribution to the regeneration of a helix structure at the time of gelation. The amino acid represented by X and Y contains a large amount of imino acid (proline and oxyproline), and it is preferable that the amino acids take up 10% to 45% of the entire sequence. In the sequence of the recombinant gelatin, a proportion of amino acid constituting the Gly-X-Y repeating structure is preferably equal to or higher than 80%, more preferably equal to or higher than 95%, and most preferably equal to or higher than 99%.

In general gelatin, among polar amino acids, charged amino acids and uncharged amino acids exist at a ratio of 1:1. Herein, the polar amino acids specifically refer to cysteine, aspartic acid, glutamic acid, histidine, lysine, asparagine, glutamine, serine, threonine, tyrosine, and arginine. Among these, uncharged polar amino acids refer to cysteine, asparagine, glutamine, serine, threonine, and tyrosine. In the recombinant gelatin used in the present invention, a proportion of polar amino acids in the entirety of the constituent amino acids is 10% to 40% and preferably 20% to 30%. Furthermore, a proportion of uncharged amino acids in the polar amino acids is equal to or higher than 5% and less than 20% and preferably less than 10%. In addition, it is preferable that the amino acid sequence does not contain any one amino acid or two or more amino acids among serine, threonine, asparagine, tyrosine, and cysteine.

Generally, regarding a polypeptide, a minimum amino acid sequence is known that acts as a cell-adhesive signal (for example, "Pathologic Physiology" published from Nagai Shuppan Co., Ltd., Vol. 9, No. 7 (1990), p. 527). It is preferable that the recombinant gelatin used in the present invention has two or more cell-adhesive signals in a single molecule. Because there are many types of cells to which the signals adhere, the specific sequences thereof are expressed by one-letter amino acid notation and preferably include the sequences such as an RGD sequence, an LDV sequence, an REDV sequence, a YIGSR sequence, a PDSGR sequence, an RYVVLPR sequence, an LGTIPG sequence, an RNIAEIIKDI sequence, an IKVAV sequence, an LRE sequence, a DGEA sequence, and an HAV sequence. Among these, an RGD sequence, a YIGSR sequence, a PDSGR sequence, an LGTIPG sequence, an IKVAV sequence, and an HAV sequence are more preferable, and an RGD sequence is particularly preferable. As the RDG sequence, an ERGD sequence is preferable. By using the recombinant gelatin having the cell-adhesive signal, it is possible to increase the amount of matrix produced by cells. For example, in a case where chondrogenic differentiation is performed using mesenchymal stem cells as cells, the production of glycosaminoglycan (GAG) can be improved.

Regarding the disposition of the RDG sequence in the recombinant gelatin used in the present invention, it is preferable that the number of amino acids between RGD sequences is non-uniform, which is 0 to 100 and preferably 25 to 60.

From the viewpoint of cell adhesion•growth properties, the number of the minimum amino acid sequences contained in a single protein molecule is preferably 3 to 50, more preferably 4 to 30, particularly preferably 5 to 20, and most preferably 12.

In the recombinant gelatin used in the present invention, a ratio of an RGD motif to the total number of amino acids is preferably at least 0.4%. In a case where the recombinant gelatin contains 350 or more amino acids, it is preferable that each stretch of 350 amino acids contains at least one RGD motif. The ratio of the RGD motif to the total number of amino acids is more preferably at least 0.6%, even more preferably at least 0.8%, still more preferably at least 1.0%, yet more preferably at least 1.2%, and most preferably at least 1.5%. The number of RGD motifs in the recombinant peptide is, per 250 amino acids, preferably at least 4, more preferably 6, even more preferably 8, and still more preferably equal to or greater than 12 and equal to or less than 16. The ratio of 0.4% of the RGD motif corresponds to the fact that there is at least one RGD sequence per 250 amino acids. Because the number of RGD motifs is an integer, in order to satisfy the ratio of 0.4%, the gelatin consisting of 251 amino acids should contain at least two RGD sequences. In the recombinant gelatin of the present invention, the number of RGD sequences contained in 250 amino acids is preferably at least 2, more preferably at least 3, and even more preferably at least 4. In another aspect of the recombinant gelatin of the present invention, the number of RGD motifs contained is at least 4, preferably 6, more preferably 8, and even more preferably equal to or greater than 12 and equal to or less than 16.

The recombinant gelatin may be partially hydrolyzed.

It is preferable that the recombinant gelatin used in the present invention is represented by Formula: A-[(Gly-X-$Y_n$)]$_m$-B. n X's each independently represent a certain amino acid, n Y's each independently represent a certain amino acid. m is preferably 2 to 10, and more preferably 3 to 5. n is preferably 3 to 100, more preferably 15 to 70, and most preferably 50 to 65. A represents a certain amino acid or amino acid sequence, B represents a certain amino acid or amino acid sequence, n X's each independently represent a certain amino acid, and n Y's each independently represent a certain amino acid.

It is more preferable that the recombinant gelatin used in the present invention is represented by Formula: Gly-Ala-Pro-[(Gly-X-Y)$_{63}$]$_3$-Gly (in the formula, 63 X's each independently represent a certain amino acid, 63 Y's each independently represent a certain amino acid, and 63 Gly-X-Y sequences may be the same as or different from each other).

The repeating unit is preferably obtained by binding a plurality of sequence units of naturally occurring collagen. The naturally occurring collagen mentioned herein is not particularly limited as long as it exists in the nature. The naturally occurring collagen is preferably type I, type II, type III, type IV, or type V collagen, and more preferably type I, type II, or type III collagen. As another form, the collagen is preferably derived from a human being, a cow, a pig, a mouse, or a rat, and more preferably derived from a human being.

The number of isoelectric points of the recombinant gelatin used in the present invention is preferably 5 to 10, more preferably 6 to 10, and even more preferably 7 to 9.5.

It is preferable that the recombinant gelatin has not undergone deamination.

It is preferable that the recombinant gelatin does not have a telopeptide.

It is preferable that the recombinant gelatin is a substantially pure polypeptide prepared by a nucleic acid encoding an amino acid sequence.

The recombinant gelatin used in the present invention is particularly preferably (1) a peptide having an amino acid sequence described in SEQ ID NO: 1; (2) a biocompatible peptide having an amino acid sequence obtained by the deletion, substitution, or addition of one or plural amino acids in the amino acid sequence described in SEQ ID NO: 1; or (3) a biocompatible peptide having an amino acid sequence which shares a sequence identity of equal to or higher than 80% (more preferably equal to or higher than 90%, particularly preferably equal to or higher than 95%, and most preferably equal to or higher than 98%) with the amino acid sequence described in SEQ ID NO: 1.

In "amino acid sequence obtained by the deletion, substitution, or addition of one or plural amino acids", "one or plural amino acids" means that the number of amino acids is preferably 1 to 20, more preferably 1 to 10, even more preferably 1 to 5, and particularly preferably 1 to 3.

The recombinant gelatin used in the present invention can be manufactured by gene recombination techniques known to those in the related art. For example, the recombinant gelatin can be manufactured based on the methods described in EP1014176A2, U.S. Pat. No. 6,992,172, WO2004/85473, WO2008/103041, and the like. Specifically, a gene encoding an amino acid sequence of specific recombinant gelatin is obtained and incorporated into a recombinant expression vector so as to prepare a recombinant expression vector, and the vector is introduced into an appropriate host so as to prepare a transformant. By culturing the obtained transformant in an appropriate medium, recombinant gelatin is produced. Therefore, by recovering the produced recombinant gelatin from the culture, the recombinant gelatin used in the present invention can be prepared.

(1-4) Biocompatible Polymer Block

In the present invention, a block (mass) formed of the aforementioned biocompatible polymer is used.

In the present invention, the shape of the biocompatible polymer block is not particularly limited. For example, the block has an amorphous shape, a spherical shape, a particle (granule) shape, a powder shape, a porous shape, a fiber shape, a spindle shape, a flat shape, and a sheet shape, and preferably has an amorphous shape, a spherical shape, a particle (granule) shape, a powder shape, and a porous shape. The amorphous shape means that the surface shape of the block is not uniform, and is, for example, the shape of a substance having irregularities such as a rock.

In the present invention, the size of a single biocompatible polymer block is not particularly limited, but is preferably equal to or greater than 1 μn) and equal to or less than 1,000 μm, more preferably equal to or greater than 10 μm and equal to or less than 1,000 μm, even more preferably equal to or greater than 10 μm and equal to or less than 700 μm, still more preferably equal to or greater than 10 μn) and equal to or less than 300 μm, yet more preferably equal to or greater than 10 μm and equal to or less than 200 μm, more preferably equal to or greater than 20 μm and equal to or less than 200 μm, even more preferably equal to or greater than 20 μm and 150 μm, and still more preferably equal to or greater than 50 μm and equal to or less than 110 μm. It is preferable that the size of a single biocompatible polymer block is within the above range, because then the tubular structure has higher molecular permeability. The size of a single biocompatible polymer block does not mean that the average of the sizes of a plurality of biocompatible polymer blocks is within the above range; rather, it means the size of each biocompatible polymer block obtained by sieving the plurality of biocompatible polymer blocks.

The size of a single block can be defined by the size of a sieve used at the time of classifying the blocks. For example, sieving is performed using a 180 μm sieve, and then the blocks passing though the sieve are sieved through a 106 μm sieve. At this time, the blocks remaining on the sieve can be regarded as blocks having a size of 106 to 180 μm. Then, sieving is performed using a 106 μm sieve, and the blocks passing through the sieve are sieved through a 53 μm sieve. At this time, the blocks remaining on the sieve can be regarded as blocks having a size of 53 to 106 μm. Thereafter, sieving is performed using a 53 μm sieve, and the blocks passing through the sieve are sieved through a 25 μm sieve. At this time, the blocks remaining on the sieve can be regarded as blocks having a size of 25 to 53 μm.

(1-5) Method for Manufacturing Biocompatible Polymer Blocks

The method for manufacturing biocompatible polymer blocks is not particularly limited. For example, by pulverizing a porous substance of the biocompatible polymer by using a pulverizer (such as a new power mill), granular biocompatible polymer blocks can be obtained.

At the time of manufacturing the porous substance of the biocompatible polymer, by performing a freezing step in which the temperature of the solution of the portion with the highest temperature in the solution (maximum internal solution temperature) becomes equal to or lower than "melting point of solvent—3° C." in an unfrozen state, the formed ice becomes spherical. Because the ics is dried through this step, a spherical porous substance having isotropic pores (spherical pores) is obtained. By freezing the ices without performing the freezing step in which the temperature of the solution of the portion with the highest temperature in the solution (maximum internal solution temperature) becomes equal to or lower than "melting point of solvent—3° C." in an unfrozen state, the formed ice becomes cylindrical/flat plate. If the ice is dried through this step, a cylindrical or flat plate-like porous substance having pores (cylindrical/flat plate-like pores) that extend uniaxially or biaxially is obtained.

In the present invention, biocompatible polymer blocks can be preferably manufactured by a method including a step a of freezing a solution of a biocompatible polymer by a freezing treatment in which a maximum internal solution temperature as a temperature of the solution of a portion with the highest temperature in the solution becomes equal to or lower than a temperature 3° C. lower than a melting point of a solvent ("melting point of solvent—3° C.") in an unfrozen state; and a step b of freeze-drying the frozen biocompatible polymer obtained in the step a.

In the present invention, a granular biocompatible polymer blocks can be more preferably manufactured by pulverizing a porous substance obtained by the step b.

The solution of a biocompatible polymer can be more preferably frozen in the step a by a freezing treatment in which a maximum internal solution temperature as a temperature of the solution of a portion with the highest temperature in the solution becomes equal to or lower than a temperature 7° C. lower than a melting point of a solvent ("melting point of solvent—7° C.") in an unfrozen state.

(2) Cell

Any cells can be used in the present invention as long as they can be transplanted. The type of cells is not particularly limited, and can be selected according to the use of the tubular structure. One kind of cells may be used, or plural kinds of cells may be used in combination. The cells to be used are preferably animal cells, more preferably vertebrate-derived cells, and particularly preferably human-derived cells. The type of the vertebrate-derived cells (particularly, human-derived cells) may be any of totipotent cells, somatic stem cells, progenitor cells, and adult cells. As the totipotent cells, for example, it is possible to use embryonic stem (ES) cells, germline stem (GS) cells, or induced pluripotent stem (iPS) cells. As the somatic stem cells, for example, it is possible to use mesenchymal stem cells (MSC), hematopoietic stem cells, amniotic cells, cord blood-derived cells, bone marrow-derived cells, myocardial stem cells, adipose-derived stem cells, or neural stem cells. As the progenitor cells and the adult cells, for example, it is possible to use cells derived from the skin, dermis, epidermis, muscles, cardiac muscles, nerves, bones, cartilage, endothelium, brain, epithelium, heart, kidney, liver, pancreas, spleen, oral cavity, cornea, bone marrow, cord blood, amnion, or hair. As the human-derived cells, for example, it is possible to use ES cells, iPS cells, MSC, chondrocytes, osteoblasts, osteoprogenitor cells, mesenchymal cells, osteoblasts, myocardial cells, cardiac myoblasts, nerve cells, hepatocytes, beta cells, fibroblasts, corneal endothelial cells, vascular endothelial cells, corneal epithelial cells, amniotic cells, cord blood-derived cells, bone marrow-derived cells, or hematopoietic stem cells. Furthermore, the source of the cells is not limited, and the cells may be autologous or allogenic.

In the present invention, vascular cells can be preferably used. In the present specification, the vascular cells mean the cells involved in angiogenesis such as cells constituting blood vessels and blood, progenitor cells being able to be differentiated into the aforementioned cells, and somatic stem cells. Herein, the vascular cells do not include ES cells, GS cells, pluripotent cells such as iPS cells, or the cells which are not spontaneously differentiated into cells constituting blood vessels or blood such as mesenchymal stem cells (MSC). The vascular cells are preferably cells constituting blood vessels. Regarding the vertebrate-derived cells (particularly, human-derived cells), specific examples of the cells constituting blood vessels include vascular endothelial cells and vascular smooth muscle cells. The vascular endothelial cells may be venous endothelial cells and arterial endothelial cells. As the progenitor cells of vascular endothelial cells, vascular endothelial progenitor cells can be used. Among the above, vascular endothelial cells and vascular endothelial progenitor cells are preferable. As the cells constituting blood, hemocytes can be used, and it is possible to use leucocytes such as lymphocytes or neutrophils, monocytes, and hematopoietic stem cells which are stem cells of these.

In the present specification, non-vascular cells mean cells other than the aforementioned vascular cells. For example, it is possible to use ES cells, iPS cells, mesenchymal stem cells (MSC), myocardial stem cells, myocardial cells, fibroblasts, myoblasts, chondrocytes, hepatocytes, or nerve cells. It is possible to preferably use MSC, chondrocytes, myoblasts, myocardial stem cells, myocardial cells, hepatocytes, or iPS cells. Among these, MSC, myocardial stem cells, myocardial cells, or myoblasts are more preferable.

The cell structure of the present invention may contain non-vascular cells. Furthermore, the cell structure of the present invention may be constituted only with non-vascular cells. The cell structure of the present invention may contain two or more kinds of cells and may contain both of the non-vascular cells and the vascular cells.

(3) Cell Structure

In the present invention, the biocompatible polymer blocks and cells are used, the plurality of biocompatible polymer blocks is three-dimensionally disposed in the form of mosaic in voids between the plurality of cells, and in this way, a cell structure is prepared. By three-dimensionally disposing the biocompatible polymer blocks and cells in the form of mosaic, a cell structure in which the cells homogeneously exist is formed, and nutrients such as a medium component can be delivered to the inside of the cell structure from the outside.

In the cell structure used in the present invention, the plurality of biocompatible polymer blocks is disposed in the voids between the plurality of cells. Herein, the "voids between the cells" do not need to be spaces closed by the constituent cells and may be interposed between the cells. It is not necessary for all of the cells to have voids therebetween, and there may be sites where the cells contact each other. The distance between voids of the cells via the biocompatible polymer block, that is, a void distance determined when a certain cell and another cell nearest to the aforementioned cell are selected is not particularly limited. The void distance preferably equals to the size of the biocompatible polymer block, and a suitable distance is also within a range of a suitable size of the biocompatible polymer block.

The biocompatible polymer block is interposed between cells. However, it is not necessary for all of the biocompatible polymer blocks to have cells therebetween, and there may be a site where the biocompatible polymer blocks contact each other. The distance between the biocompatible polymer blocks via the cells, that is, the distance determined when a biocompatible polymer block and another biocompatible polymer block nearest to the aforementioned biocompatible polymer block are selected is not particularly limited. It is preferable that the distance equals to the size of a single cell used or to the size of a cell obtained when the several cells used are aggregated. For example, the distance is equal to or greater than 10 μm and equal to or less than 1,000 μm, preferably equal to or greater than 10 μm and equal to or less than 100 μm, and more preferably equal to or greater than 10 μm and equal to or less than 50 μm.

In the present specification, the expression of "homogeneously exist" as in "cell structure in which cells homogeneously exist" is used. However, the expression does not mean that the cells are completely homogeneous, but means that nutrients such as a medium component can be delivered to the inside of the cell structure from the outside.

The thickness or diameter of the cell structure can be set to be a desired thickness. The lower limit thereof is preferably equal to or greater than 215 μm, more preferably equal to or greater than 400 μm, and most preferably equal to or greater than 730 μm. The upper limit of the thickness or diameter is not particularly limited. For use, the upper limit is preferably within a range of equal to or less than 3 cm, more preferably equal to or less than 2 cm, and even more preferably equal to or less than 1 cm. The thickness or diameter of the cell structure is preferably within a range of equal to or greater than 400 μm and equal to or less than 3 cm, more preferably within a range of equal to or greater than 500 μm and equal to or less than 2 cm, and even more preferably within a range of equal to or greater than 720 μm and 1 cm. If the thickness or diameter of the cell structure is within the above range, a tubular structure is easily prepared using the cell structure.

It is preferable that, in the cell structure, an area formed of the biocompatible polymer blocks and an area formed of cells are disposed in the form of mosaic. In the present specification, "thickness or diameter of the cell structure" means the following. A certain point A in the cell structure is selected, and at this time, among straight lines passing through the point A, the length of a line segment dividing the cell structure such that the distance from the outside of the cell structure becomes the shortest is taken as a line segment A. In the cell structure, the point A at which the line segment A becomes the longest is selected, and at this time, the length of the line segment A is taken as "thickness or diameter of the cell structure".

In the cell structure, the ratio between the cells and the biocompatible polymer blocks is not particularly limited. However, the ratio of the biocompatible polymer blocks to a single cell is preferably equal to or higher than 0.0000001 μg and equal to or lower than 1 μg, more preferably equal to or higher than 0.000001 μg and equal to or lower than 0.1 μg, even more preferably equal to or higher than 0.00001 μg and equal to or lower than 0.01 μg, and most preferably equal to or higher than 0.00002 μg and equal to or higher than 0.006 μg. If the ratio between the cells and the biocompatible polymer blocks is within the above range, the cells can more homogeneously exist, and the ratio of the volume of the biocompatible polymer blocks to the volume of the cell structure and the ratio of the volume of the cells to the volume of the cell structure can be made fall into the range specified in the present invention. If the lower limit of the ratio is within the above range, the effects of the cells can be exerted when the cell structure is used for the purpose described above, and if the upper limit of the ratio is within the above range, the randomly existing components in the biocompatible polymer blocks can be supplied to the cells. The components in the biocompatible polymer blocks are not particularly limited, and examples thereof include components contained in a medium that will be described later.

The cell structure of the present invention may contain an angiogenetic factor. Examples of the angiogenetic factor suitably include a basic fibroblast growth factor (bFGF), a vascular endothelial growth factor (VEGF), a hapatocyte growth factor (HGF), and the like. The method for manufacturing the cell structure containing the angiogenetic factor is not particularly limited. For example, the cell structure can be manufactured using biocompatible polymer blocks impregnated with the angiogenetic factor. From the viewpoint of accelerating angiogenesis, it is preferable that the cell structure of the present invention contains the angiogenetic factor.

(4) Method for Manufacturing Cell Structure

The cell structure can be manufactured by mixing the biocompatible polymer blocks with at least one kind of cells. More specifically, the cell structure can be manufactured by alternately disposing the biocompatible polymer blocks and the cells. The manufacturing method is not particularly limited but is preferably a method of forming biocompatible polymer blocks and then seeding cells. Specifically, by incubating a mixture of biocompatible polymer blocks and a cell-containing culture solution, the cell structure can be manufactured. For example, in a liquid held in a container, cells and biocompatible polymer blocks prepared in advance are disposed in the form of mosaic. It is preferable to accelerate or control the formation of mosaic-like arrays formed of cells and a biocompatible substrate by using spontaneous coagulation, free fall, centrifugation, or stirring as means for disposition.

As the container to be used, a container formed of a poorly cell-adhesive material or a non-cell-adhesive material is preferable, and more preferably a container formed of polystyrene, polypropylene, polyethylene, glass, polycarbonate, or polyethylene terephthalate is more preferable. The bottom surface of the container preferably has a flat shape, a U-shape, or a V-shape.

(5) Tubular Structure.

The method for manufacturing the tubular structure of the present invention will be described later.

Figure 5:
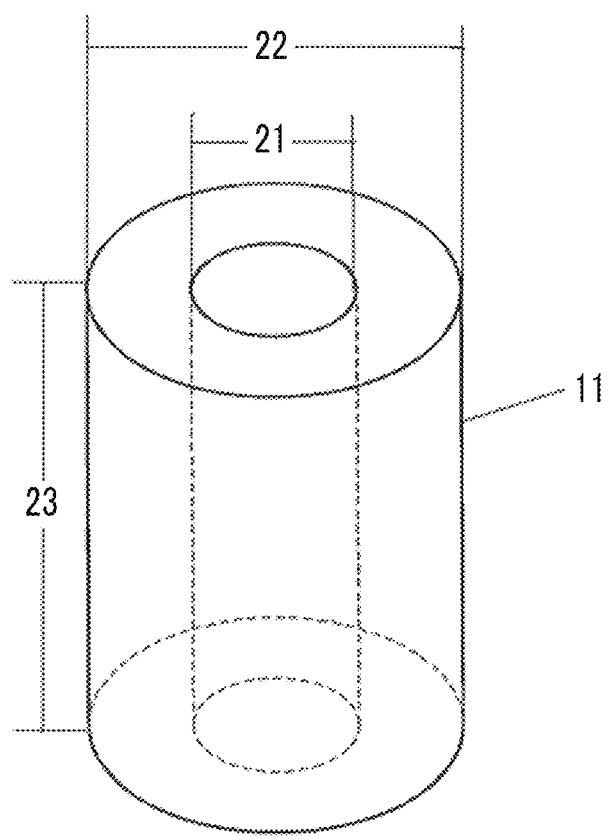
FIG. 5 shows an example of the structure of a tubular structure.

FIG. 5 is a schematic view showing a typical example of the tubular structure of the present invention. FIG. 5 shows an inner diameter 21, an outer diameter 22, and a length 23 of the tubular structure. The tubular structure of the present invention has a structure in which an approximately cylindrical cavity is on the inside of an approximately cylindrical structure. Here, the cross-sectional shape thereof is not limited to a precise circle, and may be a shape such as an ellipse that is analogous a circle.

The size of the tubular structure of the present invention is not particularly limited, and can be designed as desired according to the purpose.

In a case where the tubular structure is considered to be used as an artificial blood vessel, the inner diameter of the tubular structure of the present invention is preferably equal to or greater than 1 mm and less than 6 mm, more preferably equal to or greater than 1 mm and equal to or less than 5 mm, and even more preferably equal to or greater than 1 mm and equal to or less than 3 mm.

In a case where the tubular structure is considered to be used as an artificial blood vessel, the outer diameter of the tubular structure of the present invention is preferably equal to or greater than 3 mm and equal to or less than 10 mm, more preferably equal to or greater than 3 mm and equal to or less than 8 mm, and even more preferably equal to or greater than 3 mm and equal to or less than 5 mm.

From the viewpoint of the strength of the tubular structure and the like, the difference between the inner diameter and the outer diameter is preferably equal to or greater than 1 mm and equal to or less than 9 mm, and more preferably equal to or greater than 2 mm and equal to or less than 5 mm.

In a case where the tubular structure is considered to be used as an artificial blood vessel, the length of the tubular structure of the present invention is preferably equal to or greater than 5 mm and equal to or less than 300 mm, and more preferably equal to or less than 5 mm and equal to or less than 150 mm.

Herein, the inner diameter and the outer diameter mean an inner diameter and an outer diameter obtained in a case where the cross-section of the tubular structure of the present invention is approximated to a circle.

(6) Use of Tubular Structure

The tubular structure of the present invention can be used as an artificial blood vessel, an artificial ureter, an artificial digestive tract, and the like, and can be preferably used as an artificial blood vessel. Specifically, for example, the cell structure of the present invention can be used for being transplanted into a site in need of transplantation of an artificial blood vessel, an artificial ureter, or an artificial digestive tract.

As the transplantation method, incision or an endoscope can be used.

According to the present invention, there is provided a transplantation method including a step of transplanting the tubular structure into a patient in need of transplantation of an artificial blood vessel. In the transplantation method of the present invention, the aforementioned tubular structure of the present invention is used. The suitable scope of the cell structure and the tubular structure is the same as described above.

According to the present invention, there is also provided a use of the tubular structure of the present invention that is for manufacturing an artificial blood vessel. The suitable scope of the cell structure and the tubular structure is the same as described above.

[Method for Manufacturing Tubular Structure]

The cell structure (mosaic cell mass) obtained by (4) Method for manufacturing cell structure described above makes it possible to manufacture the tubular structure of the present invention having a desired size, by a method such as (a) fusion of cell structures (mosaic cell masses) with each other or (b) increasing the volume in a differentiation medium or a growth medium. The fusion method and the volume increasing method are not particularly limited, but it is preferable to use a method of fusing the cell structures with each other by culturing the plurality of cell structures, in which biocompatible polymer blocks are disposed in voids of a plurality of cells, in a device having a mold for forming a tubular structure. The device having a mold for forming a tubular structure will be described later.

In a case where the cell structures are fused, for example, it is possible to fuse a plurality of cell structures which contains a plurality of biocompatible polymer blocks and a plurality of cells and in which one or plural biocompatible polymer blocks described above are disposed in a portion or all of a plurality of voids formed by the plurality of cells.

The suitable scopes of "biocompatible polymer blocks (type, size, or the like)", "cells", "void between cells", "obtained cell structure (size or the like), "ratio between cells and biocompatible polymer blocks", and the like relating to the method for manufacturing the tubular structure of the present invention are the same as described above in the present specification.

The thickness or diameter of each cell structure before fusion described above is preferably equal to or greater than 10 μm and equal to or less than 1 cm, more preferably equal to or greater than 10 μm and equal to or less than 2,000 μm, even more preferably equal to or greater than 15 μm and equal to or less than 1,500 μm, and most preferably equal to or greater than 20 μm and equal to or less than 1,300 μm. The thickness or diameter of the fused cell structure is preferably equal to or greater than 400 μm and equal to or less than 3 cm, more preferably equal to or greater than 500 μm and equal to or less than 2 cm, and even more preferably equal to or greater than 720 μm and equal to or less than 1 cm.

[Device for Manufacturing Tubular Structure]

The present invention also relates to a device for manufacturing the aforementioned tubular structure of the present invention, which includes a base portion that has a cylindrical hollow area for forming an external lateral surface of a tubular structure constituted with a cell structure, a core receiving portion that is on the inside of the hollow area, and a cylindrical core portion that is for forming an internal lateral surface of the tubular structure.

Each of the cylindrical shape, the flat surface, and the perpendicular direction mentioned in the present specification does not mean a precise cylinder, a precise flat surface, and a precise perpendicular direction, and includes an approximately cylindrical shape, an approximately flat surface, and an approximately perpendicular direction. The approximately cylindrical shape means that the cylindrical shape may be deformed, and includes a shape having an elliptical top or bottom surface. The approximately flat surface means that the flat surface has small irregularities or is slightly bent in some cases. The approximately perpendicular direction means that, provided that the angle of the perpendicular direction is 90° C., the angle may includes an error of ±10°, preferably includes an error of ±5°, and more preferably includes an error of ±2°.

Hereinafter, the device of the present invention will be described with reference to FIGS. 1 to 4.

FIGS. 1 and 2 show an example of the structure of a base portion 1. FIGS. 1A and 2A are top views, FIGS. 1B and 2B are front views, FIGS. 1C and 2C are lateral views, FIGS. 1D and 2D are bottom views, and FIGS. 1E and 2E are perspective views.

The base portion 1 has a cylindrical hollow area 2 for forming an external lateral surface of a tubular structure constituted with a cell structure.

A top surface 5 of the base portion 1 is a flat surface, and the hollow area 2 is provided from the top surface 5 of the base portion along a direction perpendicular to the flat surface as the top surface of the base portion.

There is a difference in the diameter of the hollow area between the base portion shown in FIG. 1 and the base portion shown in FIG. 2. The diameter of the hollow area of the base portion shown in FIG. 2 is greater than the diameter of the hollow area of the base portion shown in FIG. 1.

The diameter of the cylindrical shape of the hollow area corresponds to the outer diameter of the tubular structure, and can be set according to the outer diameter of the tubular structure to be manufactured. The diameter of the cylindrical shape of the hollow area is not particularly limited, and for example, can be set to be equal to or greater than 3 mm and equal to or less than 10 mm, preferably can be set to be equal to or greater than 3 mm and equal to or less than 8 mm, and more preferably can be set to be equal to or greater than 3 mm and equal to or less than 5 mm.

The total size of the base portion is not particularly limited as long as the base portion is large enough for the hollow area having the aforementioned size to be able to be provided. For example, regarding the size of the top surface, the length is equal to or greater than 5 mm and equal to or less than 300 mm, preferably equal to or greater than 10 mm and equal to or less than 200 mm, and more preferably equal to or greater than 10 mm and equal to or less than 100 mm, and the width is equal to or greater than 5 mm and equal to or less than 300 mm, preferably equal to or greater than 10 mm and equal to or less than 200 mm, and more preferably equal to or greater than 10 mm and equal to or less than 100 mm. The height of the base portion is not particularly limited, and for example, equal to or greater than 5 mm and equal to or less than 300 mm, preferably equal to or greater than 10 mm and equal to or less than 300 mm, and more preferably equal to or greater than 10 mm and equal to or less than 200 mm.

The diameter of the cylindrical shape of the hollow area is greater than the diameter of the cylindrical shape of the core portion which will be described later, because at least a portion of the core portion exists in the hollow area.

In the base portion 1 shown in FIGS. 1 and 2, the hollow area 2 penetrates the base portion from the top surface 5 to the bottom surface.

The bottom surface of the base portion has a structure in which, when the base portion is installed in a container containing a medium, a medium component contained in the medium can enter the inside of the hollow area of the base portion from an inlet on a bottom surface side of penetration areas of a core receiving portion which will be described later. Specific examples of the aforementioned structure include a case where the bottom surface of the base portion is shaped to have an area 8, which contacts an installation surface when the base portion is installed on the installation surface, and an area 9 which does not contact the installation surface. The area which does not contact the installation surface is an area spaced from a grounding surface.

In the embodiments shown in FIGS. 1 and 2, when viewed from front (see FIGS. 1B and 1C), the bottom surface of the base portion has a recessed shape. By being caused to have a recessed shape, the bottom surface has the area 8 which contacts the installation surface and the area 9 which does not contact the installation surface. However, as long as the area 8 which contacts the installation surface and the area 9 which does not contact the installation surface can be provided, the shape of the bottom surface is not limited to the recessed shape.

FIG. 3 shows an example of the structure of a core receiving portion 3. FIG. 3A is a top view, FIG. 3B is a front view, FIG. 3C is a lateral view, and FIG. 3D is a perspective view.

The core receiving portion 3 is provided on the inside of the hollow area 2 of the base 1. In FIGS. 1 and 2, the base 1 and the core receiving portion 3 are separately illustrated. However, the base 1 and the core receiving portion 3 may be integrally formed in a state of being provided on the inside of the hollow area 2 of the core receiving portion 3 and the base 1. Alternatively, after the base 1 and the core receiving portion 3 are separately prepared, the core receiving portion 3 may be installed on the inside of the hollow area 2 of the base 1, and then the device may be used.

In a case where the core receiving portion 3 is provided on the inside of the hollow area 2, a tubular structure is formed by a space surrounded by the top surface of the core receiving portion and the wall surface of the hollow area 2.

It is preferable that the core receiving portion 3 is provided at a lower end 10 of the hollow area or in the vicinity of the lower end 10 of the hollow area.

The shape of the core receiving portion 3 is not particularly limited as long as the shape can held a core portion 4 and is formed on the inside of the hollow area 2 of the base 1. It is preferable that the core receiving portion 3 has a cylindrical shape having a through hole 6 for holding the core portion in the central portion and one or more penetration areas 7, which penetrate the core receiving portion from the top surface to the bottom surface thereof, in the peripheral portion.

From the viewpoint of holding the core portion, it is preferable that the shape of the through hole 6 is approximately the same as the shape of the core portion. The shape of the through hole 6 is preferably cylindrical. The diameter of the cylinder is not particularly limited and can be set to be, for example, equal to or greater than 1 mm and less than 6 mm, preferably can be set to be equal to or greater than 1 mm and equal to or less than 5 mm, and more preferably can be set to be equal to or greater than 1 mm and equal to or less than 3 mm.

It is preferable that the core receiving portion 3 has a total size and a shape that enable the core receiving portion 3 to be installed on the inside of the hollow area 2.

The core receiving portion 3 shown in FIG. 2 has 4 penetration areas 7. However, the number of the penetration areas 7 is not particularly limited, and can be arbitrarily set as long as the number is equal to or greater than 1. Generally, the number of the penetration areas is about 1 to 8, and preferably about 2 to 6. By providing the penetration areas 7, when the base portion is installed in a container containing a medium, a medium component contained in the medium can enter the inside of the hollow area of the base portion from an inlet on the bottom surface side of the penetration areas of the core receiving portion. For the purpose described above, it is preferable that the inlet on the bottom surface side of the penetration areas 7 of the core receiving portion is provided in the area 9 which does not contact the installation surface within the bottom surface of the base portion.

By setting the diameter of the through hole 6 for holding the core portion in the central portion to be approximately the same as the diameter of the core portion, the core receiving portion 3 can hold the core portion 4.

FIG. 4 shows an example of the structure of the core portion 4. FIG. 4A is a top view, FIG. 4B is a front view, and FIG. 4C is a perspective view. It is preferable that the core portion 4 has a cylindrical shape. The core portion 4 is for forming a cavity of the tubular structure (that is, the inner wall of the tubular structure) of the cell structure. By causing the core portion 4 to have a cylindrical shape, a tubular structure (generally having a cylindrical cavity) can be manufactured.

The core portion 4 is held by the core receiving portion 3, and at least a portion of the core portion 4 is provided in the hollow area 2 along a direction perpendicular to a direction of the flat surface of the base portion.

In FIGS. 3 and 4, the core receiving portion 3 and the core portion 4 are separately illustrated. However, the core receiving portion 3 and the core portion 4 may be integrally formed in a state where the core portion 4 is inserted into the through hole 6 of the core receiving portion 3. Alternatively, after the core receiving portion 3 and the core portion 4 are separately prepared, the core portion 4 may be inserted into the through hole 6 of the core receiving portion 3, and then the device may be used.

As described above, the base 1 and the core receiving portion 3 may be integrally formed or separately prepared.

Accordingly, examples of aspects of the device of the present invention include the following.

(1) An aspect in which the base portion, the core receiving portion, and the core portion are integrally formed;

(2) an aspect in which the base portion and the core receiving portion are integrally formed, the core portion is separately formed, the core portion is held in the core receiving portion in the integrally formed base portion and the core receiving portion, and then the device is used;

(3) an aspect in which the base portion, the core receiving portion, and the core portion are separately formed, these three members are combined as described above in the present specification, and then the device is used; and (4) another aspect in which the base portion 1 is constituted with two or more members.

Figure 1E:
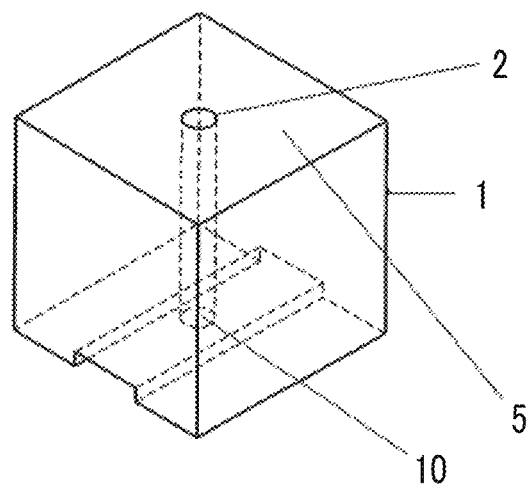
Figure 2A:
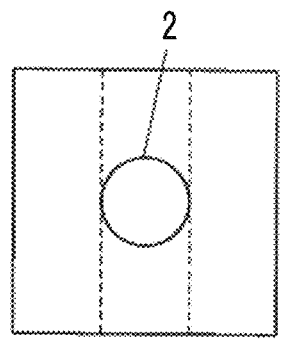
FIGS. 2A-2E show another example of the structure of a base portion.
Figure 2E:
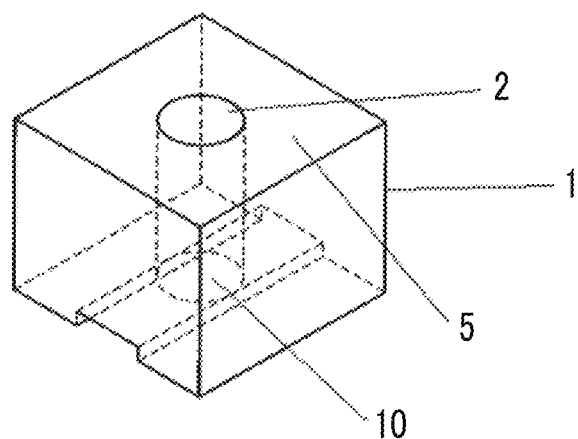
Figure 2B:
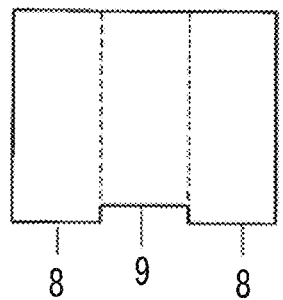
Figure 2C:
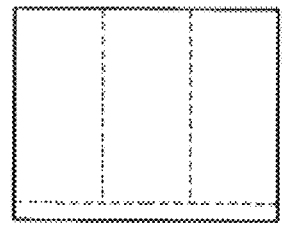
Figure 2D:
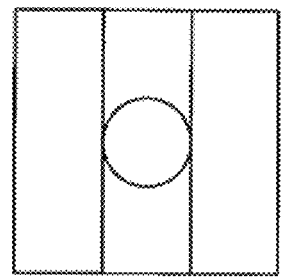
Figure 3A:
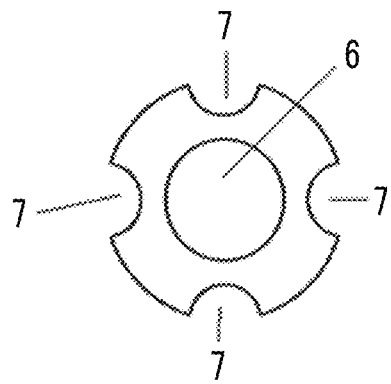
FIGS. 3A-3D show an example of the structure of a core receiving portion.
Figure 3C:
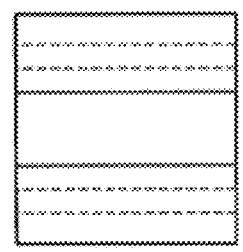
Figure 3B:
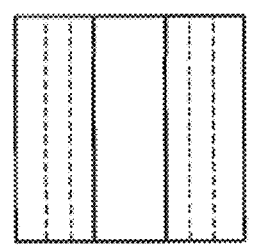
Figure 3D:
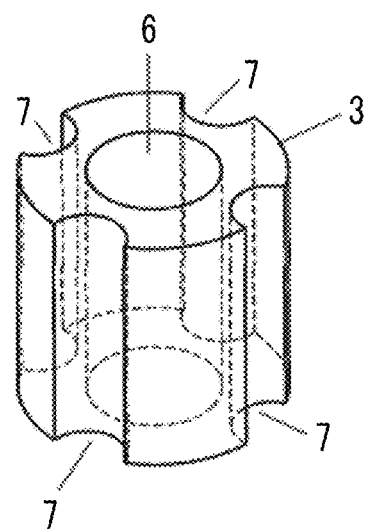

For example, in FIGS. 1E and 2E which are perspective views of the base portion 1, the upper end portion and the lower end portion of the base portion can be separately formed and then laminated, and then the device can be used.

The center of the diameter of the cylindrical shape of the hollow area 2 is approximately the same as the center of the diameter of the cylindrical shape of the core portion 4.

The diameter of the cylindrical shape of the core portion 4 is smaller than the diameter of the cylindrical shape of the hollow area 2.

The diameter of the cylindrical shape of the core portion corresponds to the inner diameter of the tubular structure. The diameter of the cylindrical shape of the core portion can be set according to the inner diameter of the tubular structure to be manufactured. The diameter of the cylindrical shape of the core portion is not particularly limited, and can be set to be, for example, equal to or greater than 1 mm and less than 6 mm, preferably can be set to be equal to or greater than 1 mm and equal to or less than 5 mm, and more preferably can be set to be equal to or greater than 1 mm and equal to or less than 3 mm.

The length of the core portion is not particularly limited, and is generally about equal to or greater than 10 mm and equal to or less than 300 mm and preferably equal to or greater than 10 mm and equal to or less than 150 mm.

The device of the present invention including the base portion, the core receiving portion, and the core portion can be manufactured using any material. For example, the device can be manufactured using silicon, a fluororesin, polytetrafluoroethylene (PTFE), perfluoroalkoxyalkane (tetrafluoroethylene.perfluoroalkylvinyl ether copolymer) (PFA), a perfluoroethylene propylene copolymer (tetrafluoroethylene.hexafluoropropylene copolymer) (FEP), TEFLON (registered trademark), polystyrene, polypropylene, polyethylene, glass, polycarbonate, polyethylene terephthalate, a metal, stainless steel, aluminum, and the like. Among these, a poorly cell-adhesive material or a non-cell-adhesive material is the most preferable.

Preferably, the core portion and/or the portion forming the hollow area can have a hollow mesh shape. Although the tubular structure of the cell structure contacts the core portion and/or the portion forming the hollow area, by making the core portion and/or the portion forming the hollow area have a hollow mesh shape, the medium components can be incorporated into the cell structure. As a result, at the time of manufacturing the tubular structure by culturing the cell structure, the medium component can be more easily supplied to the cells. Examples of the hollow mesh-like structure include a structure established by preparing the core portion by using a bundle of hollow fiber.

Hereinafter, the present invention will be more specifically described based on examples, but the present invention is not limited to the examples.

EXAMPLES

[Example 1] Recombinant Peptide (Recombinant Gelatin)

As a recombinant peptide (recombinant gelatin), the following CBE3 was used (described in WO2008/103041A)
CBE3:
Molecular weight: 51.6 kD
Structure: GAP [(GXY)$_{63}$]$_3$G
Number of amino acids: 571
RDG sequences: 12
Imino acid content: 33%
Almost 100% of the amino acids are GXY repeating structures. The amino acid sequence of CBE3 does not include serine, threonine, asparagine, tyrosine, and cysteine. CBE3 has an ERGD sequence.
Isoelectric points: 9.34
GRAVY value: −0.682
1/IOB value: 0.323
Amino acid sequence (SEQ ID NO: 1 of the sequence list) (the same as SEQ ID NO: 3 in WO2008/103041A; here, the terminal X is changed to "P")

GAP(GAPGLQGAPGLQGMPGERGAAGLPGPKGERGDAGPKGADGAPGAPGL

QGMPGERGAAGLPGPKGERGDAGPKGADGAPGKDGVRGLAGPIGPPGERGA

AGLPGPKGERGDAGPKGADGAPGKDGVRGLAGPIGPPGAGAPGAPGLQGM

PGERGAAGLPGPKGERGDAGPKGADGAPGKDGVRGLAGPP)3G

[Example 2] Preparation of Porous Substance of Recombinant Peptide

[Thick Cylindrical PTFE Container]
A cylindrical cup-like container made of polytetrafluoroethylene (PTFE) having a bottom surface thickness of 3 mm, a diameter of 51 mm, a lateral surface thickness of 8 mm, and a height of 25 mm was prepared. When the lateral surface of the cylindrical cup-like container made of PTFE is made into a curved surface, the lateral surface is closed by 8 mm PTFE, and the (flat circular plate-like) bottom surface of the container is also closed by 3 mm PTFE. In contrast, the top surface of the container is opened. Accordingly, the inner diameter of the cylindrical cup-like container is 43 mm. Hereinafter, this container will be referred to as a thick cylindrical PTFE container.

An aqueous CBE3 solution was caused to flow into the thick cylindrical PTFE container and cooled from the bottom surface in a vacuum freeze drier (TF5-85ATNNN: manufactured by TAKARA Co., Ltd.) by using a cooling tray. The final concentration of the aqueous CBE3 solution was 4% by mass, and the amount of the aqueous solution was 8 mL. The temperature of the tray was cooled down to −10° C., and the solution was frozen for 1 hour at −10° C., then for 2 hours at −20° C., subsequently for 3 hours at −40° C., and finally for 1 hour at −50° C. Thereafter, the temperature of the tray was reset to be −20° C., and then the obtained frozen product was dried in a vacuum for 24 hours at −20° C. After 24 hours, in a state where the frozen product was being continuously dried in a vacuum, the temperature of the tray was increased to 20° C., and the frozen product was further dried in a vacuum for 48 hours at 20° C. until a degree of vacuum was sufficiently reduced (1.9×10$^5$ Pa) and then taken out of the vacuum freeze drier. In this way, a porous substance was obtained.

At the time of preparing the porous substance, each aqueous solution is cooled from the bottom surface. Therefore, cooling the temperature of water surface in the central portion of the circle is the most difficult. Accordingly, because the temperature of the portion of water surface in the central portion of the circle becomes the highest in the solution, the temperature of the solution of the portion of water surface in the central portion of the circle was measured. Hereinafter, the temperature of the solution of the portion of water surface in the central portion of the circle will be referred to as a maximum internal solution temperature.

Figure 6:
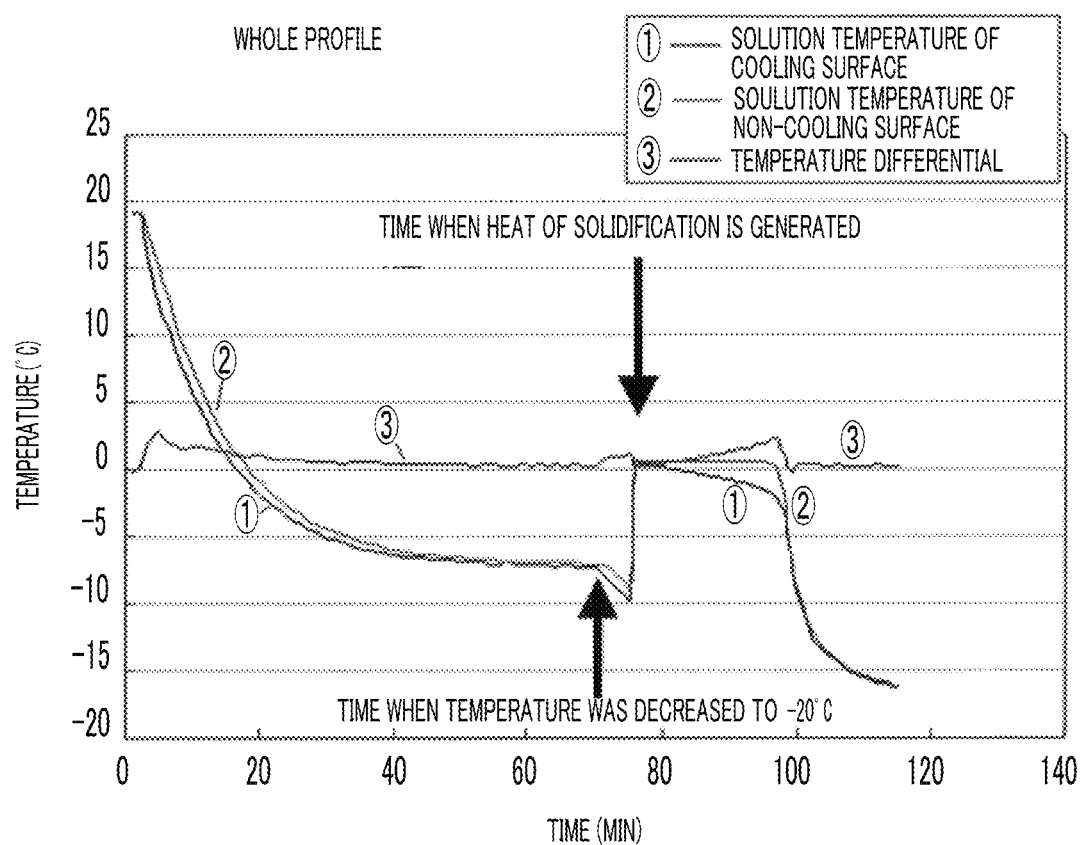
FIG. 6 shows a temperature profile at the time of freezing a solvent in examples.

[Example 3] Measurement of Maximum Internal Solution Temperature in Freezing Step FIG. 6 shows a temperature profile at the time of freezing a solvent. After an unfrozen state at a temperature of equal to or lower than a melting point, heat of solidification is generated. As a result, the temperature starts to increase, and at this stage, the formation of ice is actually started. Thereafter, the temperature stays around 0° C. for a certain period of time, and at this stage, water and ices are in a state of mixture. Finally, the temperature starts again to decrease from 0° C., and at this stage, the liquid portion disappears, and only ice exists. The temperature measured at this stage is not the solution temperature but the solid temperature of the inside of the ice. As described above, by checking the maximum internal solution temperature at the moment when the heat of solidification is generated, it is possible to figure out whether the solution is frozen after the maximum internal solution temperature passes through "melting point of solvent—3° C." in the unfrozen state.

The maximum internal solution temperature in the unfrozen state at the moment when the heat of solidification was generated was −8.8° C. By checking the maximum internal solution temperature at the moment when the heat of solidification is generated, it is possible to figure out that the maximum internal solution temperature is equal to or lower than "melting point of solvent—3° C." in the unfrozen state.

[Example 4] Preparation of Recombinant Peptide Blocks (Pulverizing and Cross-Linking Porous Substance)

The CBE3 porous substance obtained in Example 2 was pulverized using a new power mill (manufactured by Osaka Chemical Co., Ltd., NEW POWER MILL PM-2005). The pulverization was performed 5 times for 1 minute at a maximum rotation frequency, and hence the pulverization was performed for a total of 5 minutes. The obtained pulverized substances were classified according to their size by using a sieve made of stainless steel, thereby obtaining granular CBE3 blocks having sizes of 25 to 53 μm, 53 to 106 μm, and 106 to 180 μm. Then, the blocks were subjected to thermal cross-linking at 160° C. under nitrogen (cross-linking time: 8 to 48 hours), thereby obtaining recombinant peptide blocks. In the following section, only the blocks having a size of 53 to 106 μm were used.

[Example 5] Preparation of Cell Structure by Using Recombinant Peptide Blocks (Human Bone Marrow-Derived Mesenchymal Stem Cells (hMSC))

Human bone marrow-derived mesenchymal stem cells (hMSC) were seeded in a growth medium (TAKARA BIO INC: MSCGM BulletKit (registered trademark)) at 100,000 cells/mL, and the CBE3 blocks (53 to 106 μm) prepared in Example 4 were added thereto at 0.1 mg/mL. 100 μL of the obtained mixture was seeded in a SUMILON CELLTIGHT X96U plate (Sumitomo Bakelite Co., Ltd., U-shaped bottom), subjected to centrifugation by using a microplate centrifuge (600 g, 5 minutes), and allowed to stand for 24 hours, thereby preparing a spherical cell structure having a diameter of 0.75 mm and formed of the CBE3 blocks and hMSC cells (0.001 μg of blocks per cell). The cell structure was spherical because it was prepared in the U-shaped plate.

[Example 6] Preparation of Tubular Structure by Using Cell Structure

By putting the cell structure prepared in Example 5 into a special casting device, a tubular structure formed of a plurality of cell structures was prepared.

A casting device A (for inner diameter of 1 mm and an outer diameter of 3 mm) made of silicon constituted with the members shown in FIGS. 1, 3, and 4 and a casting device B (for an inner diameter of 3 mm and an outer diameter of 5 mm) made of silicon constituted with the members shown in FIGS. 2, 3, and 4 were prepared.

Figure 1B:
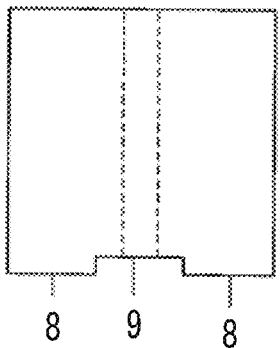
Figure 1C:
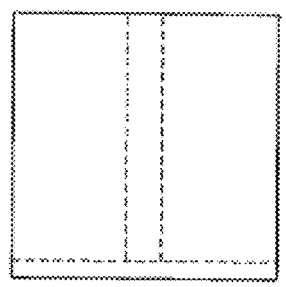
Figure 1D:
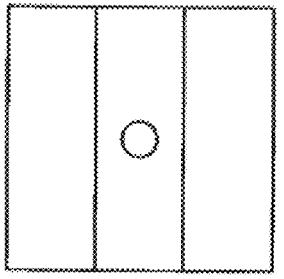

The diameter of the hollow area of the base portion (FIG. 1) of the casting device A is 3 mm. The top surface (FIG. 1A) of the base portion of the casting device A is 15 mm (length)×15 mm (width) square. The height (height of the portion 8 in FIG. 1B) of the base portion is 13 mm, and the height of the portion 9 in FIG. 1B is 12 mm.

The top surface (FIG. 3A) of the core receiving portion (FIG. 3) of the casting device A has such a shape that a circle having a diameter of 1 mm is cut out from the center of a circle having a diameter of 3 mm, and semicircles having a diameter of 1 mm are cut out from 4 sites of the peripheral portion of the circle having a diameter of 3 mm. The height of the core receiving portion is 3 mm.

The core portion (FIG. 4) of the casting device A is a cylinder having a diameter of 1 mm and a length of 17 mm.

The diameter of the hollow area of the base portion (FIG. 2) of the casting device B is 5 mm. The top surface (FIG. 1A) of the base portion of the casting device A is 15 mm (length)×15 mm (width) square. The height (height of the portion 8 in FIG. 1B) of the base portion is 13 mm, and the height of the portion 9 in FIG. 1B is 12 mm.

The top surface (FIG. 3A) of the core receiving portion (FIG. 3) of the casting device B has such a shape that a circle having a diameter of 3 mm is cut out from the center of a circle having a diameter of 5 mm, and semicircles having a diameter of 1 mm are cut out from 4 sites of the peripheral portion of the circle having a diameter of 5 mm. The height of the core receiving portion is 3 mm.

The core portion (FIG. 4) of the casting device B is a cylinder having a diameter of 3 mm and a length of 17 mm.

The three portions consisting of the base portion (FIGS. 1 and 2), the core receiving portion (FIG. 3), and the core portion (FIG. 4) were separately prepared from a silicon ingot by cutting processing and combined into the casting device at the time of use. Particularly, in order to increase viability of cells in advance by increasing the diffusivity of the solution in the process of preparing the tubular structure, draining holes are opened in the core receiving portion of the lower base (depressions at 4 sites in the core receiving portions). When the aforementioned portions were combined, the core receiving portion was inserted into the portion of through hole of the base such that the lower surface of the base and the lower surface of the core receiving portion formed the same plane. Furthermore, a core was installed in the hole of the central portion of the core receiving portion. As a result, in the upper portion of the core receiving portion, a space is made which formed of the core, the inner wall of the through hole of the base, and the upper surface of the core receiving portion. The cell structure can be installed in the space. Three hundred eighty four cell structures prepared in Example 5 were set in the present devices as casting devices having an inner diameter of 1 mm and an outer diameter of 3 mm (consequently, the length became 8 mm), and 600 cell structures prepared in Example 5 were set in the present devices as casting devices having an inner diameter of 3 mm and an outer diameter of 5 mm (consequently, the length became 7 mm). The casting devices finished with setting were cultured for 3 days in a state of being immersed into a medium (TAKARA BIO INC: MSCGM BulletKit (registered trademark)).

Figure 7:
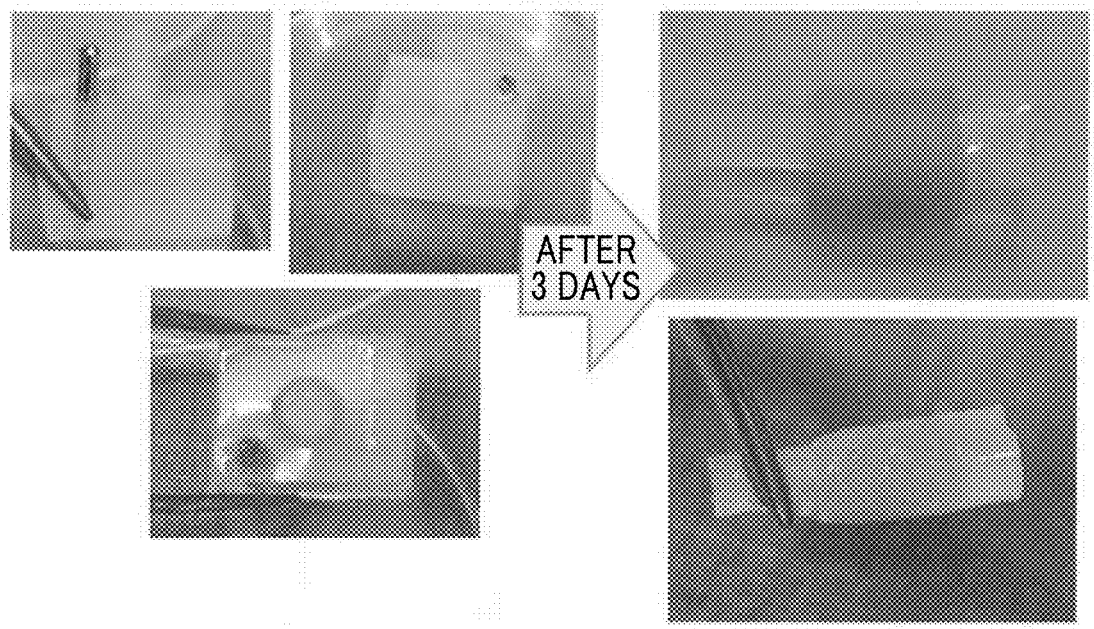
FIG. 7 shows a tubular structure detached from a device.
Figure 8:
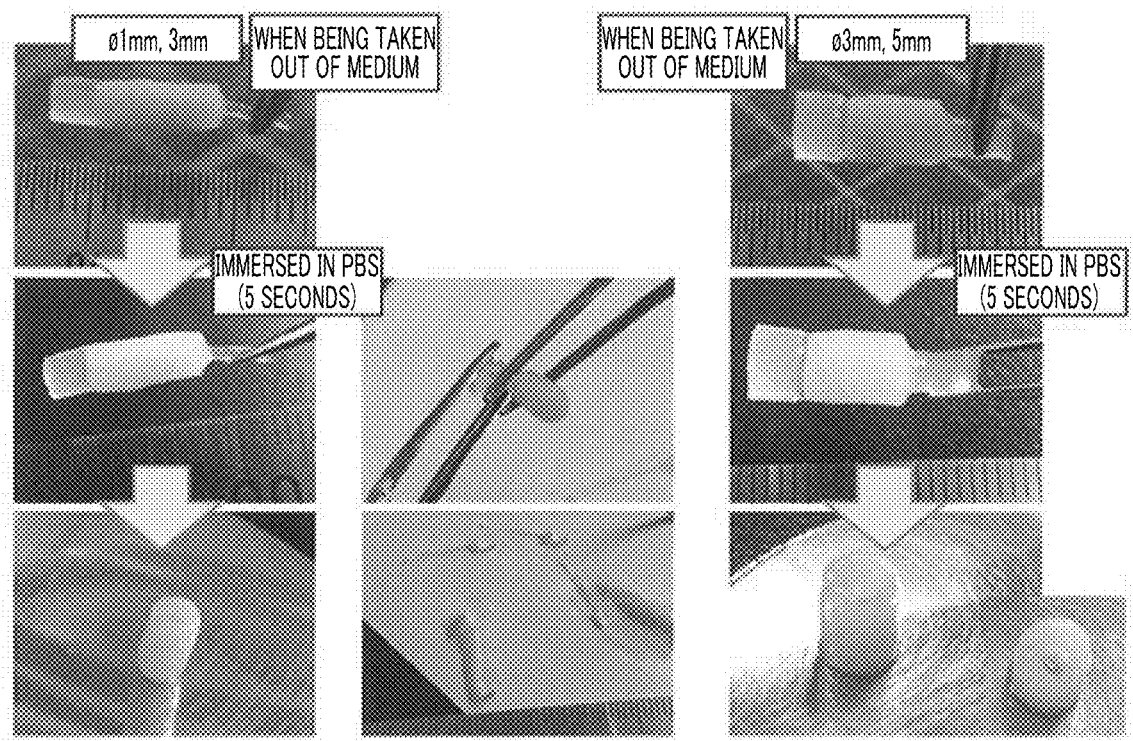
FIG. 8 shows the way the tubular structure is cultured for 3 weeks and detached from the core portion.

Then, the cores of the casting devices and the cell structures were detached from the outer frame of the devices, thereby obtaining tubular structures with the cores that were constituted with the cell structures (for example, the tubular structures had an inner diameter of 1 mm, an outer diameter of 3 mm, and a length of 8 mm or had an inner diameter of 3 mm, an outer diameter of 5 mm, and a length of 7 mm) (see FIG. 7). These tubular structures were cultured for 3 weeks, thereby obtaining stronger tubular structures (see FIG. 8).

[Example 7] Molecular Permeability of Wall Portion of Tubular Structure of Cell Structure The molecular permeability of the wall portion of the tubular structure of the cell structure prepared in Example 6 was evaluated by checking how well a dye comes into and out of the wall portion. The wall portion of the tubular structure of the cell structure can allow a phenol red (molecular weight: 354.38) component in the medium to extremely excellently permeate wall portion. Therefore, when the tubular structure is taken out of the medium, the wall portion thereof appears red (see the top section of FIG. 8). When the tubular structure is moved into a transparent solution such as PBS, the phenol red in the wall portion is instantaneously diffused, and the red color comes out (see the middle section of FIG. 8). This shows that the molecular permeability of the wall portion of the tubular structure is markedly high.

Figure 9:
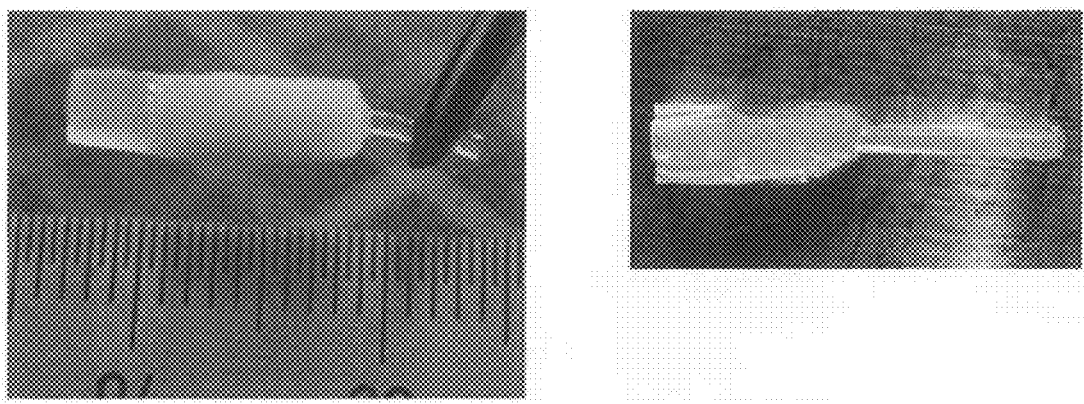
FIG. 9 shows the results of comparison between the molecular permeability of a wall portion of a tubular structure (drawing on the left side) of the present invention and the molecular permeability of a wall portion of a tubular structure (drawing on the right side) formed only of cells.
Figure 10:
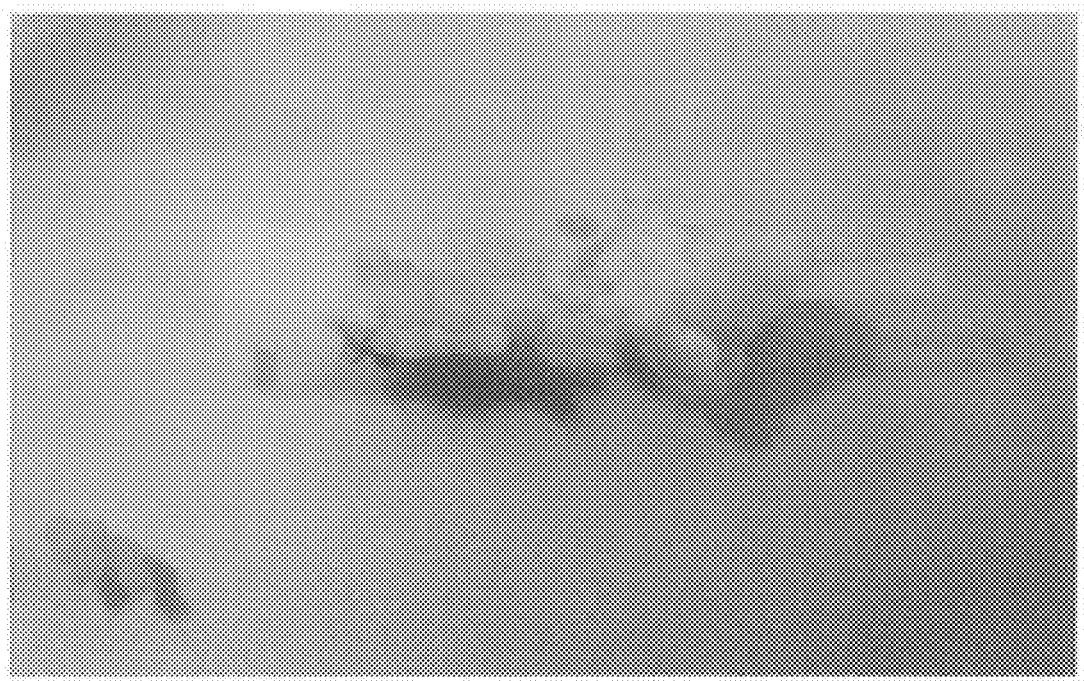
FIG. 10 shows the way the tubular structure prepared using only cells is broken.

Meanwhile, in a case where the same tubular structure is prepared using only cells, the wall portion of the tubular structure does not allow phenol red in the medium to permeate the wall portion, and hence the wall portion does not appear red (image on the right side of FIG. 9). This shows that the molecular permeability thereof is markedly low.

The above results prove that the wall portion of the tubular structure of the cell structure of the present invention prepared in Example 6 has molecular permeability extremely higher than that of the tubular structure formed only of cells.

Comparative Example 1

Tubular structures formed only of cells were prepared in the same manner as in Examples 5 and 6, except that recombinant peptide blocks were not used. As a result, it was found that it is extremely difficult for the structures formed

Figure 11:
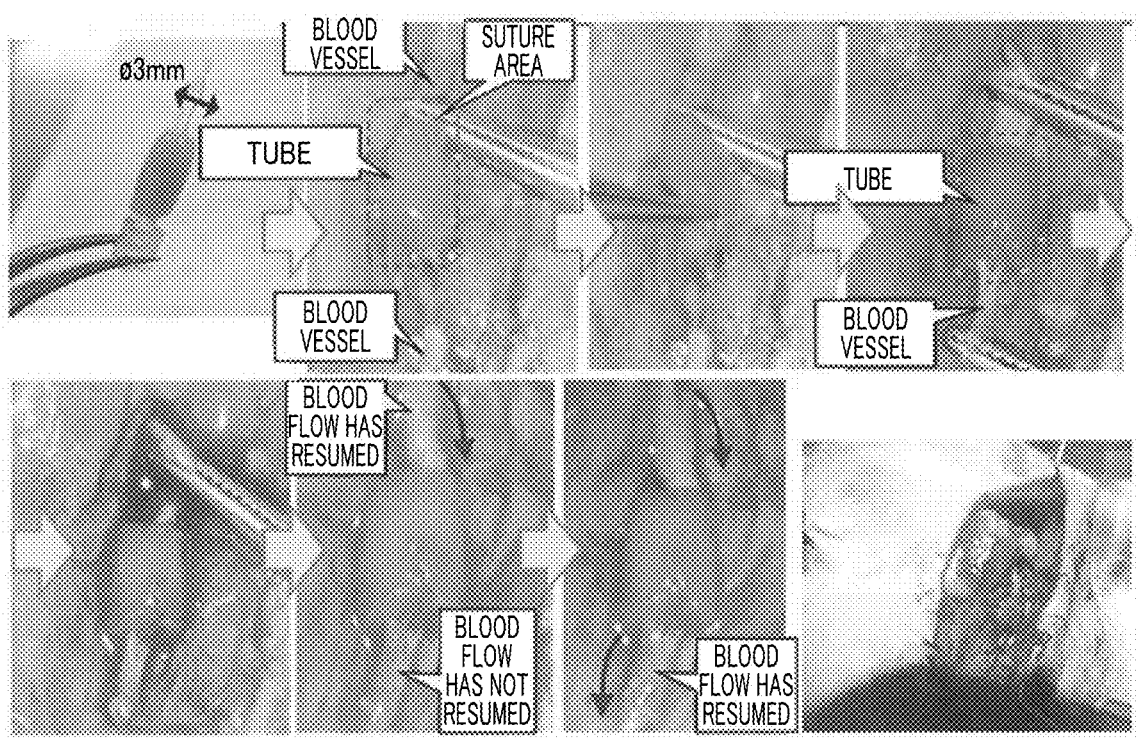
FIG. 11 shows the results obtained by transplanting a tubular structure into the jugular vein of a hairless rat and checking functioning of the tubular structure as a blood vessel.

[Example 8] Transplantation of Tubular Structure Constituted with Cell Structure into Rat Jugular Vein The tubular structures of the cell structures prepared in Example 6 were transplanted into the jugular vein of a hairless rat by anastomosis. The procedure was performed on a hairless rat (male, 9-week-old) under anesthesia (isoflurane). First, an incision was made in the skin of the neck of the rat from the chest side such that the left and right jugular veins were exposed, and then an adherent tissue was detached such that a jugular vein was exposed. The jugular vein was clamped at two sites consisting of the central side and the peripheral side such that the blood flow was stopped, the blood vessel was cut, and the external membrane of the periphery of the blood vessel was detached. Under a microscope, the tubular structure of the cell structure prepared in Example 6 was transplanted into the cut portion of the blood vessel by suturing by using 10-0 suture thread. Subsequently, the clamp on the peripheral side was removed, and then the clamp on the central side was removed with checking the recovery of blood flow. When bleeding stopped, the patency of the blood vessel was checked. As a result, it was possible to confirm that the transplanted tubular structure of the cell structure was patent (FIG. 11).

From the above result, it was understood that, surprisingly, the tubular structure of the cell structure according to the present invention has strength and flexibility that enable suturing. Furthermore, it was understood that the tubular structure of the cell structure according to the present invention can be connected through anastomosis to a blood vessel derived from a biological body, does not cause blood to leak from the anastomotic portion, and enables blood to flow in the tubular structure.

As described above, it was possible to confirm that the tubular structure of the present invention can function as a tubular structure a biological tissue requires.

EXPLANATION OF REFERENCES

1: base portion
2: hollow area
3: core receiving portion
4: core portion
5: top surface
6: through hole
7: penetration area
8: area contacting installation surface
9: area which does not contact installation surface
10: lower end of hollow area
11: tubular structure
21: inner diameter
22: outer diameter
23: length

What is claimed is:

1. A tubular structure comprising:
a cell structure containing a plurality of biocompatible polymer blocks and processed naturally occurring cells,
wherein the plurality of polymer blocks is disposed in voids between the plurality of processed naturally occurring cells, and
wherein the tubular structure has an inner diameter of equal to or greater than 1 mm and less than 6 mm, an outer diameter of equal to or greater than 3 mm and equal to or less than 10 mm, and a length of equal to or greater than 5 mm and equal to or less than 300 mm.

2. The tubular structure according to claim 1 that is an artificial blood vessel.

3. The tubular structure according to claim 1,
wherein the cell structure contains the biocompatible polymer blocks in an amount of equal to or greater than 0.0000001 µg and equal to or less than 1 µg per cell.

4. The tubular structure according to claim 1,
wherein each of the biocompatible polymer blocks has a size of equal to or greater than 10 µm and equal to or less than 300 µm.

5. The tubular structure according to claim 1,
wherein the biocompatible polymer blocks are formed of a recombinant peptide.

6. The tubular structure according to claim 5,
wherein the recombinant peptide is any one of a peptide having an amino acid sequence described in SEQ ID NO: 1; a biocompatible peptide having an amino acid sequence obtained by the deletion, substitution, or addition of one or plural amino acids in the amino acid sequence described in SEQ ID NO: 1; or a biocompatible peptide having an amino acid sequence which shares a sequence identity of equal to or higher than 80% with the amino acid sequence described in SEQ ID NO: 1.

7. The tubular structure according to claim 6,
wherein the biocompatible polymer blocks are in the form of granules obtained by pulverizing a porous substance of the biocompatible polymer.

8. The tubular structure according to claim 5,
wherein in the biocompatible polymer blocks, the biocompatible polymer is cross-linked by heat, ultraviolet rays or an enzyme.

9. The tubular structure according to claim 5,
wherein the biocompatible polymer blocks are in the form of granules obtained by pulverizing a porous substance of the biocompatible polymer.

10. The tubular structure according to claim 1,
wherein in the biocompatible polymer blocks, the biocompatible polymer is cross-linked by heat, ultraviolet rays or an enzyme.

11. The tubular structure according to claim 1,
wherein the biocompatible polymer blocks are in the form of granules obtained by pulverizing a porous substance of the biocompatible polymer.

12. A device for manufacturing the tubular structure according to claim 1, comprising:
a base portion that has a cylindrical hollow area for forming an external lateral surface of a tubular structure constituted with a cell structure;
a core receiving portion that exists on the inside of the hollow area; and
a cylindrical core portion that is for forming an inner lateral surface of the tubular structure,
wherein a top surface of the base portion is a flat surface,
the hollow area is provided from the top surface of the base portion along a direction perpendicular to the flat surface as the top surface of the base portion,
the core portion is held by the core receiving portion,
at least a portion of the core portion is provided in the hollow area along a direction perpendicular to a direction of the flat surface of the base portion,
the center of a diameter of the cylindrical shape of the hollow area is the same as the center of a diameter of the cylindrical shape of the core portion,
the diameter of the cylindrical shape of the core portion is smaller than the diameter of the cylindrical shape of the hollow area,
the core receiving portion has a through hole for holding the core portion in a central portion thereof and has one or more penetration areas, which penetrate the core receiving portion from a top surface to a bottom surface, in a peripheral portion thereof, and
a bottom surface of the base portion has a structure in which, when the base portion is installed in a container containing a medium, a medium component contained in the medium can enter the inside of the hollow area from an inlet on a bottom surface side of the penetration areas of the core receiving portion.

13. The device according to claim 12,
wherein the bottom surface of the base portion has a shape having an area which contacts an installation surface when the base portion is installed on the installation surface and an area which does not contact the installation surface, and
the inlet on the bottom surface side of the penetration areas of the core receiving portion is provided in the area which does not contact the installation surface.

14. The device according to claim 12,
wherein the diameter of the cylindrical shape of the core portion is equal to or greater than 1 mm and less than 6 mm, and
the diameter of the cylindrical shape of the hollow area is equal to or greater than 3 mm and equal to or less than 10 mm.

15. The device according to claim 12,
wherein either or both of the core portion and a portion forming the hollow area have a hollow mesh shape.

16. A method for manufacturing the tubular structure according to claim 1, comprising:
a step of fusing a plurality of cell structures in which biocompatible polymer blocks are disposed in voids of a plurality of cells.

17. The method according to claim 16,
wherein the cell structures are fused by culturing the plurality of cell structures, in which biocompatible polymer blocks are disposed in voids of a plurality of cells, in a device having a mold for forming a tubular structure.

18. The method according to claim 16,
wherein the device having a mold for forming a tubular structure, comprises:
a base portion that has a cylindrical hollow area for forming an external lateral surface of a tubular structure constituted with a cell structure;
a core receiving portion that exists on the inside of the hollow area; and
a cylindrical core portion that is for forming an inner lateral surface of the tubular structure,
wherein a top surface of the base portion is a flat surface,
the hollow area is provided from the top surface of the base portion along a direction perpendicular to the flat surface as the top surface of the base portion,
the core portion is held by the core receiving portion,
at least a portion of the core portion is provided in the hollow area along a direction perpendicular to a direction of the flat surface of the base portion,
the center of a diameter of the cylindrical shape of the hollow area is the same as the center of a diameter of the cylindrical shape of the core portion,
the diameter of the cylindrical shape of the core portion is smaller than the diameter of the cylindrical shape of the hollow area,
the core receiving portion has a through hole for holding the core portion in a central portion thereof and has one or more penetration areas, which penetrate the core receiving portion from a top surface to a bottom surface, in a peripheral portion thereof, and
a bottom surface of the base portion has a structure in which, when the base portion is installed in a container containing a medium, a medium component contained in the medium can enter the inside of the hollow area from an inlet on a bottom surface side of the penetration areas of the core receiving portion.

* * * * *